US012281340B2

(12) United States Patent
Nagata et al.

(10) Patent No.: US 12,281,340 B2
(45) Date of Patent: Apr. 22, 2025

(54) METHOD OF PRODUCING N-ACYL-AMINO GROUP-CONTAINING COMPOUND

(71) Applicant: AJINOMOTO CO., INC., Tokyo (JP)

(72) Inventors: Hidemi Nagata, Kanagawa (JP); Keiko Danjou, Kanagawa (JP); Jun Takakura, Kanagawa (JP); Hiroyuki Nozaki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 17/025,173

(22) Filed: Sep. 18, 2020

(65) Prior Publication Data

US 2021/0071214 A1 Mar. 11, 2021

Related U.S. Application Data

(63) Continuation of application No. PCT/JP2019/007681, filed on Feb. 27, 2019.

(30) Foreign Application Priority Data

Apr. 13, 2018 (JP) ................................ 2018-077741

(51) Int. Cl.

| | |
|---|---|
| ***C12P 13/00*** | (2006.01) |
| ***C12N 9/00*** | (2006.01) |
| ***C12N 9/42*** | (2006.01) |
| ***C12N 9/80*** | (2006.01) |
| ***C12P 21/00*** | (2006.01) |

(52) U.S. Cl.

CPC .......... *C12P 13/005* (2013.01); *C12N 9/2445* (2013.01); *C12N 9/80* (2013.01); *C12N 9/93* (2013.01); *C12P 21/00* (2013.01); *C12Y 302/01021* (2013.01); *C12Y 305/01014* (2013.01); *C12Y 602/0103* (2013.01)

(58) Field of Classification Search

None

See application file for complete search history.

(56) References Cited

FOREIGN PATENT DOCUMENTS

| | | | |
|---|---|---|---|
| WO | WO2008/131002 | A2 | 10/2008 |
| WO | WO2014/100525 | A2 | 6/2014 |
| WO | WO2015/028423 | A1 | 3/2015 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*

Schroeder et al. J Am Oil Chem Soc (2014), 91, 1695-1702.*

Sherp et al., Journal of Biological Chemistry, vol. 293, No. 12, pp. 4277-4288, Feb. 2018.*

Chen, Q., et al., "A liquid chromatography-tandem mass spectrometry-based assay for indole-3-acetic acid-amido synthetase," Analyt. Biochem. 2009;390:149-154.

"Pseudomonas syringae IAA-lysine synethase (iaaL) gene, complete cds." Database accession No. M35373.1, Apr. 26, 1993, 1 pg, retrieved from the internet on Jan. 1, 2022.

Roberto, F. F., et al., "Expression and fine structure of the gene encoding N epsilon-(indole-3-acetyl)-L-lysine synthetase from Pseudomonas savastanoi," PNAS 1990;87:5797-5801.

Koreishi, M., et al., "Efficient N epsilon-lauroyl-L-lysine production by recombinant epsilon-lysine acylase from Streptomyces mobaraensis," J. Biotechnol. 2009;141:160-165.

Koreishi, M., et al., "A Novel Acylase from Streptomyces mobaraensis that Efficiently Catalyzes Hydrolysis/ Synthesis of Capsaicins as well as N-Acyl-L-amino Acids and N-Acyl-peptides," J. Agric. Food Chem. 2006;54:72-78.

Brady, S. F., et al., "N-Acyl Derivatives of Arginine and Tryptophan Isolated from Environmental DNA Expressed in *Escherichia coli*," Org. Lett. 2005;7(17):3613-3616.

Westfall, C. S., et al., "Modulating plant hormones by enzyme action: the GH3 family of acyl acid amino synthetases," Plant Signal. Behav. 2010;5(12):1607-1612.

Staswick, P., et al., "Characterization of an *Arabidopsis* enzyme family that conjugates amino acids to indole-3-acetic acid," The Plant Cell 2005;17:616-627.

Database UniProt KB, Sep. 23, 2008, Accession No. B4WTV2 : GH3 auxin-responsive promoter superfamily protein from *Synechococcus* sp. (strain ATCC 29403 / PCC 7335), 1 pg.

Extended European Search Report for European Patent App. No. 19784845.0 (Jan. 4, 2022).

Wada, E., et al., "Enzymatic Synthesis of N-Acyl-L-Amino Acids in a Glycerol-Water System Using Acylase I from Pig Kidney," JAOCS 2002;79(1):41-46.

Westfall, C. S., et al., "Modulating plant hormones by enzymes action," Plant Signaling & Behavior 2010;5(12):1607-1612.

Staswick, P. E., et al., "Characterization of an *Arabidopsis* Enzyme Family That Conjugates Amino Acids to Indole-3-Acetic Acid," The Plant Cell 2005;17:616-627.

Database UniProtKB [online], Accession No. B4WTV2, <https://www.uniprot.org/uniprot/B4WTV2.txt?version=18>, Sep. 23, 2008, [retrieved on May 8, 2019], SubName: Full=GH3 auxin-responsive promoter superfamily {ECO:0000313 EMBL:EDX83115.1}, 1 pg.

(Continued)

*Primary Examiner* — Richard G Hutson

(74) *Attorney, Agent, or Firm* — Cermak & McGowan LLP; Shelly Guest Cermak

(57) ABSTRACT

A method efficiently produces a compound containing an N-acyl-amino group by an enzymatic method. Specifically, a method of producing a compound containing an N-acyl-amino group includes producing the compound containing an N-acyl-amino group by reacting a compound containing an amino group with a compound containing a carboxyl group in the presence of an enzyme having an ability to bond a carboxyl group and an amino group in an ATP dependent manner to form an amide bond.

14 Claims, No Drawings

Specification includes a Sequence Listing.

(56) References Cited

OTHER PUBLICATIONS

Roberto, F. F., et al., "Expression and fine structure of the gene encoding N epsilon-(indole-3-acetyl)-L-lysine synthetase from Pseudomonas savastanoi," Proc. Natl. Acad. Sci. USA 1990;87:5797-5801.

International Search Report and Written Opinion for PCT Patent App. No. PCT/JP2019/007681 (May 21, 2019) with English language translation of the ISR.

* cited by examiner

METHOD OF PRODUCING N-ACYL-AMINO GROUP-CONTAINING COMPOUND

This application is a Continuation of, and claims priority under 35 U.S.C. § 120 to, International Application No. PCT/JP2019/007681, filed Feb. 27, 2019, and claims priority therethrough under 35 U.S.C. § 119 to Japanese Patent Application No. 2018-077741, filed Apr. 13, 2018, the entireties of which are incorporated by reference herein. Also, the Sequence Listing filed electronically herewith is hereby incorporated by reference (File name: 2020-09-18T US-621_Seq_List; File size: 77 KB; Date recorded: Sep. 18, 2020).

TECHNICAL FIELD

The present disclosure relates to a method of producing an N-acyl-amino group-containing compound.

BACKGROUND ART

Compounds containing an N-acyl-amino group (e.g., Nα-acylamino acids) are used as materials for perfumery and cosmetics (e.g., surfactants). Chemical synthesis of the compounds containing an N-acyl-amino group (e.g., Schotten-Baumann reaction) has the problem of environmental load due to byproducts of the synthesis reaction. Thus, enzymatic synthesis of compounds containing an N-acyl-amino group is required. Several prior techniques for the enzymatic synthesis of compounds containing an N-acyl-amino group have been reported.

Patent Literature 1 reports fermentation of Nα-acylamino acids from sugar utilizing a surfactin biosynthesis enzyme from *Bacillus subtilis*. However, this fermentation is not suitable for the production on an industrial scale because the amount of Nα-acylamino acid produced is 116.8 mg/L, that is, a trace amount.

Patent Literature 2 reports a method of synthesizing Nα-acylglycine from an amino acid and a fatty acid using amino acid N-acyltransferase from human and acyl CoA synthetase from *E. coli*. However, the amino acid cannot directly be bonded to the fatty acid and an enzymatic reaction in two steps is required in this method. Thus, control becomes complicated compared to a reaction using a single enzyme.

Non-patent Literature 1 reports a method of synthesizing an Nα-acylamino acid from an amino acid and a fatty acid in a glycerol-containing solution using acylase from swine kidney. This method utilizes a phenomenon where a hydrolysis reaction of the Nα-acylamino acid by acylase is less likely to progress in the glycerol-containing solution. However, in view of requiring the use of glycerol in a large amount and there being a low yield of Nα-acylamino acid synthesis in an aqueous solvent not containing glycerol, this method is less efficient in industrial production.

Non-patent Literature 2 reports a method of synthesizing an Nα-acylamino acid from an amino acid and a fatty acid in a glycerol-containing solution using acylase from *Streptomyces mobaraensis*. However, synthesis of the Nα-acylamino acid in a solution not containing glycerol is not reported. Thus, it is not revealed whether this method is efficient or not in the industrial production.

PRIOR ART REFERENCES

Patent Literatures

Patent Literature 1: WO2008/131002
Patent Literature 2: WO2015/028423

Non-Patent Literatures

Non-patent Literature 1: Wada et al., Journal of the American Oil Chemists' Society, 2002, 79(1), pp 41-46
Non-patent Literature 2: Koreishi et al., Journal of Agricultural and Food Chemistry, 2006, 54(1), pp 72-78

SUMMARY

It is an object of the present disclosure to provide a method of efficiently producing compounds containing an N-acyl-amino group by an enzymatic method.

As a result of an extensive study, the present inventors have found that an enzyme having an ability to form an amide bond by bonding a carboxyl group and an amino group in an ATP dependent manner can efficiently produce a compound containing an N-acyl-amino group from a compound containing a carboxyl group including a fatty acid and a compound containing an amino group.

An aspect of the present disclosure includes a method of producing a compound containing an N-acyl-amino group, comprising producing the compound containing an N-acyl-amino group by reacting a compound containing an amino group with a compound containing a carboxyl group in the presence of an enzyme having an ability to bond a carboxyl group and an amino group in an ATP dependent manner to form an amide bond.

A further aspect of the present disclosure includes the method as described above, wherein said enzyme is derived from a plant or a microorganism.

A further aspect of the present disclosure includes the method as described above, wherein said enzyme is a GH3 protein.

A further aspect of the present disclosure includes the method as described above, wherein said enzyme is a GH3 protein belonging to any of group I, group II and group III.

A further aspect of the present disclosure includes the method as described above, wherein the GH3 protein is selected from the group consisting of: (A) a protein comprising an amino acid sequence selected from the group consisting of SEQ ID NOs: 1 to 9; (B) a protein comprising an amino acid sequence containing one or several amino acid substitutions, deletions, insertions or additions in the amino acid sequence selected from the group consisting of SEQ ID NOs: 1 to 9, and having an N-acylase activity; and (C) a protein comprising an amino acid sequence having 90% or more identity to the amino acid sequence selected from the group consisting of SEQ ID NOs: 1 to 9, and having an N-acylase activity.

A further aspect of the present disclosure includes the method as described above, wherein said enzyme is a PaaK protein.

A further aspect of the present disclosure includes the method as described above, wherein the PaaK protein is selected from the group consisting of: (A') a protein comprising an amino acid sequence of SEQ ID NO:10 or 11; (B') a protein comprising an amino acid sequence containing one or several amino acid substitutions, deletions, insertions or additions in the amino acid sequence of SEQ ID NO:10 or 11, and having an N-acylase activity; and (C') a protein comprising an amino acid sequence having 90% or more identity to the amino acid sequence of SEQ ID NO:10 or 11, and having an N-acylase activity.

A further aspect of the present disclosure includes the method as described above, wherein the compound containing an amino group is a compound containing an amino group having an anionic group.

A further aspect of the present disclosure includes the method as described above, wherein the compound containing an amino group is an amino acid or a peptide.

A further aspect of the present disclosure includes the method as described above, wherein the compound containing an amino group is an α-amino acid, a β-amino acid, or a γ-amino acid, or a dipeptide thereof.

A further aspect of the present disclosure includes the method as described above, wherein the amino acid is an L-amino acid or a D-amino acid.

A further aspect of the present disclosure includes the method as described above, wherein the compound containing an amino group is selected from the group consisting of: (1) an amino acid selected from the group consisting of: (a) an α-amino acid selected from the group consisting of glycine, alanine, valine, leucine, isoleucine, proline, methionine, phenylalanine, tryptophan, serine, threonine, asparagine, glutamine, tyrosine, cysteine, aspartic acid, glutamic acid, histidine, lysine and arginine; (b) β-alanine; (c) a γ-aminobutyric acid; and (d) sarcosine; (2) taurine; and (3) a dipeptide selected from the group consisting of aspartylphenylalanine, glycylglycine and alanylhistidine.

A further aspect of the present disclosure includes the method as described above, wherein the carboxyl group-containing compound is a fatty acid.

A further aspect of the present disclosure includes the method as described above, wherein the fatty acid is a fatty acid having 6 to 18 carbon atoms.

A further aspect of the present disclosure includes the method as described above, wherein the fatty acid is a fatty acid having 6 to 12 carbon atoms.

A further aspect of the present disclosure includes the method as described above, wherein the fatty acid is a saturated fatty acid.

A further aspect of the present disclosure includes the method as described above, wherein said enzyme is a purified enzyme.

A further aspect of the present disclosure includes the method as described above, wherein the reaction in the presence of said enzyme is performed using a transformed microorganism which produces said enzyme or a treated product thereof.

A further aspect of the present disclosure includes the method as described above, wherein said transformed microorganism is any microorganism of the following (i) to (iii): (i) a microorganism comprising a heterologous expression unit containing a polynucleotide encoding said enzyme and a promoter operably linked thereto; (ii) a microorganism comprising an expression unit containing a polynucleotide encoding said enzyme and a promoter operably linked thereto in a non-natural genomic region or a non-genomic region; or (iii) a microorganism comprising a polynucleotide encoding said enzyme in multiple copy number in an expression unit.

A further aspect of the present disclosure includes the method as described above, wherein said microorganism is a bacterium belonging to Enterobacteriaceae.

A further aspect of the present disclosure includes the method as described above, wherein said bacterium is *Escherichia coli.*

According to a method of the present disclosure, the reaction of producing the compound containing an N-acyl-amino group can efficiently be performed by forming the amide bond between the compound containing an amino group and the compound containing a carboxyl group.

DETAILED DESCRIPTION OF THE EMBODIMENTS

The present disclosure provides a method of producing a compound containing an N-acyl-amino group. The method of the present disclosure includes producing the compound containing an N-acyl-amino group by reacting a compound containing an amino group with a compound containing a carboxyl group in the presence of an enzyme.

The enzyme used for the method of the present disclosure has an ability to form an amide bond by reacting a carboxyl group and an amino group in an ATP dependent manner. The enzyme used for the method of the present disclosure is believed to form the amide bond by a mechanism where the enzyme activates a compound containing a carboxyl group by adenylation and a compound containing an amino group attacks this adenylated intermediate in a neutrophilic manner.

The enzyme used for the method of the present disclosure may be derived from any plants and microorganisms. The plants which the enzyme used for the method of the present disclosure is derived from include plants belonging to Gymnospermae, Angiospermae, Pteridophyta, Lycopodiophyta, Anthocerotophyta, Bryophyta, Marchantiophyta, Charophyceae, Conjugatophyceae, Chlorophyta, Glaucophyta, and Rhodophyta. More specifically, the plants include those belonging to genus *Arabidopsis* (e.g., *Arabidopsis thaliana*), genus *Oryza* (e.g., *Oryza sativa*), genus *Capsicum* (e.g., *Capsicum chinense*), genus *Glycine* (e.g., *Glycine max*), genera *Solanum* or *Lycopersicon* (e.g., *Solanum lycopersicumor Lycopersicon esculentum*), genus *Nicotiana* (e.g., *Nicotiana tabacum*), genus *Physcomitrella* (e.g., *Physcomitrella patens*), genera *Citrus* (e.g., *Citrus madurensis*), genus *Pinus* (e.g., *Pinus pinaster*), genus *Brassica* (e.g., *Brassica napus*), genus *Gossypium* (*Gossypium* sp.), genus *Vitis* (e.g., *Vitis vinifera*), genus *Medicago* (e.g., *Medicago truncatula*), genus *Populus*, genus *Triticum* (e.g., *Triticum aestivium*), genus *Zea* (e.g., *Zea mays*), genus *Hordeum* (e.g., *Hordeum vulgare*), and genus *Sorghum* (e.g., *Sorghum bicolor*). Microorganisms which the enzyme used for the method of the present disclosure is derived from include those belonging to genus *Cystobacter* (e.g., *Cystobacter fuscus*), genus *Synechococcus* (e.g., *Synechococcus* sp.), genus *Pantoea* (e.g., *Pantoea agglomerans*), and genus *Pseudomonas* (e.g., *Pseudomonas savastanoi*).

The enzyme used for the method of the present disclosure may be a GH3 protein. The "GH3 protein" refers to an enzyme group that functions on amidation of plant hormones containing a carboxyl group such as jasmonic acid, auxins (indole-3-acetate), salicylic acid and substituted benzoate, and homologs thereof. The "GH3 protein" refers to proteins containing a GH3 superfamily domain as a structural characteristic. The GH3 superfamily domain is searchable from those defined in sequence database, and searchable, for example, as a protein having a domain defined as "GH3 superfamily" on the Conserved domain database of National Center for Biotechnology Information (NCBI).

Of the GH3 proteins, the GH3 proteins from the plants can especially be classified into groups I, II and III based on sequence similarity and substrate specificity (J. Biol. Chem., 2010, 285, 29780-29786, Plant Cell., 2005, 17(2). 616-627).

Group I is an enzyme group found as enzymes primarily using jasmonic acid as a substrate. The enzymes belonging to Group I include, for example, enzymes (e.g., AtGH3-10, AtJAR1 [also referred to as AtGH3-11]) from *Arabidopsis* (*Arabidopsis thaliana*), enzymes (e.g., OsAK071721, OsBAA96221) from rice (*Oryza sativa*), enzymes (e.g., LeBTO13697, LeU144810) from tomatoes (*Lycopersicon esculentum*), and an enzyme (e.g., PpABO61221) from *Physcomitrella patens.*

Group II is an enzyme group found as enzymes primarily using indole acetic acid or salicylic acid as a substrate. The enzymes belonging to Group II include, for example, enzymes (e.g., AtGH3-1, AtGH3-2, AtGH3-3, AtGH3-4, AtGH3-5, AtGH3-6, AtGH3-9, AtGH3-17) from *Arabidopsis* (*Arabidopsis thaliana*), enzymes (e.g., OsBAB63594, OsBAB92590, OsGH3-8 [also referred to as OsBAC79627]) from rice (*Oryza sativa*), an enzyme (e.g., CcAY525089) from chili pepper (*Capsicum chinense*), an enzyme (e.g., GmGH3) from soybeans (*Glycine max*), an enzymes (e.g., LeBT013446) from tomatoes (*Lycopersicon esculentum*), and an enzyme (e.g., NtAF123503) from tobacco (*Nicotiana tabacum*).

Group III is an enzyme group found as enzymes primarily using substituted benzoate as a substrate. The enzymes belonging to Group III include, for example, enzymes (e.g., AtGH3-7, AtGH3-8, AtGH3-12, AtGH3-13, AtGH3-14, AtGH3-15, AtGH3-16, AtGH3-18, AtGH3-19) from *Arabidopsis* (*Arabidopsis thaliana*).

Of the GH3 proteins, the GH3 proteins from the microorganisms include, for example, an enzyme (e.g., CfHP [WP 002626336]) from *Cystobacter fuscus*, and an enzyme (e.g., SsGH3 [GH3 auxin responsive promoter superfamily]) from *Synechococcus* sp.

The GH3 protein may be the following:

(A) a protein including an amino acid sequence from SEQ ID NOs: 1 to 9;

(B) a protein including an amino acid sequence containing one or several amino acid substitutions, deletions, insertions or additions in the amino acid sequence from SEQ ID NOs: 1 to 9, and having an N-acylase activity; or (C) a protein including an amino acid sequence having 90% or more identity to the amino acid sequence from SEQ ID NOs: 1 to 9, and having an N-acylase activity.

The enzyme used for the method of the present disclosure may be a PaaK protein. The "PaaK protein" refers to an enzyme group having a function to convert phenyl acetate to phenyl acetate CoA, and homologs thereof. The "PaaK protein" contains a PaaK superfamily domain as a structural characteristic. The PaaK superfamily domain is searchable from those defined in sequence database, and searchable, for example, as a protein having a domain defined as "PaaK superfamily" on the Conserved domain database of NCBI. The PaaK protein is sometimes found as a homolog of the GH3 protein in the sequence database, and may have, for example, 10% or more, 15% or more, 20% or more, 25% or more, and 30% or more amino acid sequence identity to the GH3 protein.

The PaaK protein includes, for example, indole acetate-lysine synthetase (IAAL) that bonds lysine to indole acetate. For example, it includes an enzyme (e.g., PsIAAL) from *Pseudomonas savastanoi*, and an enzyme (e.g., PaHP [WP_031591948]) from *Pantoea agglomerans.*

The PaaK protein may be the following:

(A') a protein including an amino acid sequence of SEQ ID NO:10 or 11;

(B') a protein including an amino acid sequence containing one or several amino acid substitutions, deletions, insertions or additions in the amino acid sequence of SEQ ID NO:10 or 11, and having an N-acylase activity; or (C') a protein including an amino acid sequence having 90% or more identity to the amino acid sequence of SEQ ID NO:10 or 11, and having an N-acylase activity.

In the protein (B) and (B'), one or several amino acid residues can be modified by 1, 2, 3 or 4 mutations from among deletions, substitutions, additions and insertions of amino acid residues. The mutations of amino acid residues may be introduced into one region, or into multiple different regions in an amino acid sequence. The term "one or several" denotes the number that does not greatly impair an activity of a protein. The number represented by the term "one or several" is, for example, 1 to 50, 1 to 40, 1 to 30, 1 to 20, 1 to 10, or 1 to 5 (e.g., 1, 2, 3, 4 or 5).

In the proteins (C) and (C'), the percent identity to the amino acid sequence selected from among SEQ ID NOs: 1 to 9 or the amino acid sequence of SEQ ID NO: 10 or 11 is 90% or more. The identity may be 91% or more, 92% or more, 93% or more, 94% or more, 95% or more, 96% or more, 97% or more, 98% or more, or 99% or more. The identity between the polypeptides (proteins) can be calculated by the algorithm blastp. More specifically, the percent identity between the polypeptides can be calculated using Scoring Parameters (Matrix: BLOSUM62; Gap Costs: Existence=11 Extension=1; Compositional Adjustments: Conditional compositional score matrix adjustment) with default settings in the algorithm blastp provided in NCBI. The percent identity between the polynucleotides (genes) can be calculated by the algorithm blastn. More specifically, the percent identity between the polynucleotides can be calculated using Scoring Parameters (Match/Mismatch Scores=1, -2; Gap Costs=Linear) with default settings in the algorithm blastn provided in NCBI.

The "N-acylase activity" refers to an activity to produce a compound containing an N-acyl-amino group using a compound containing an amino group and a compound containing a carboxyl group as substrates. For the GH3 proteins and the PaaK proteins, the proteins of (A) to (C) and (A') to (C') have the N-acylase activity, and thus, can produce the compound containing an N-acyl-amino group from a compound containing an amino group and a compound containing a carboxyl group. The proteins of (B), (B'), (C) and (C') each may have, for example, 60% or more, 70% or more, 80% or more, 85% or more, 90% or more, 94% or more, 96% or more, 98% or more or equivalent (i.e., 100%) activity based on the activity of the protein (A) or (A') corresponding to an original amino acid sequence, when the activity is measured under a certain measurement condition. The following condition can be employed as such a certain measurement condition. The protein of (A) or (A') (hereinafter referred to as a "wild type enzyme") and the protein (B), (B'), (C) or (C') (hereinafter referred to as a "modified enzyme") are prepared as purified enzymes, 0.2 mL of a reaction solution containing 50 mM Tris-HCl, and 5 mM amino acid (e.g., glycine, L-glutamic acid, L-aspartic acid), 5 mM sodium fatty acid (e.g., sodium caprylate, sodium caprate, sodium laurate), 10 mM ATP, 10 mM $MgCl_2$, 1 mM DTT, 50 μg/mL of the purified enzyme, pH 8.0 is incubated at 25° C. for 24 hours. After completion of the reaction, 0.8 mL of a reaction stopping solution (1% (v/v) phosphoric acid, 75% methanol) is added, and the mixture is filtrated through a filter followed by being subjected to UPLC-MS analysis to evaluate an N-acylase activity by measuring a signal of a molecular weight corresponding to an N-acylamino acid (e.g., Nα-capryloylglycine, Nα-caprinoylglycine, Nα-lauroylglycine, Nα-capryloyl-L-glutamic acid, Nα-caprinoyl-L-glutamic acid, Nα-lauroyl-L-glutamic acid, Nα-capryloyl-L-aspartic acid, Nα-caprinoyl-L-aspartic acid, or Nα-lauroyl-L-aspartic acid).

In the proteins (B), (B'), (C) and (C'), a mutation may be introduced into a site within a catalytic domain and a site other than the catalytic domain provided that the target property can be retained. A position of an amino acid residue that can retain the target property and to which the mutation may be introduced is obvious to a person skilled in the art. Specifically, a person skilled in the art (1) can compare amino acid sequences of multiple proteins having a similar type of property, (2) can reveal relatively conserved regions and relatively not conserved regions, then (3) can predict regions capable of playing a functionally important role and regions incapable of playing a functionally important role from the relatively conserved regions and the relatively not conserved regions, respectively, and thus, can recognize correlativity between structures and functions. Therefore, a person skilled in the art can identify the position of the amino acid residue to which the mutation may be introduced in the amino acid sequence of the protein used in the present disclosure.

When an amino acid residue is mutated by substitution, the substitution of the amino acid residue may be a conservative substitution. As used herein, the term "conservative substitution" refers to substitution of a certain amino acid residue with an amino acid residue having a similar side chain. Families of amino acid residues having the similar side chain are well-known in the art. For example, such families include amino acids having a basic side chain (e.g., lysine, arginine, histidine), amino acids having an acidic side chain (e.g., aspartic acid, glutamic acid), amino acids having an uncharged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a position β branched side chain (e.g., threonine, valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). Preferably, the conservative substitution of amino acids may be the substitution between aspartic acid and glutamic acid, the substitution between arginine and lysine and histidine, the substitution between tryptophan and phenylalanine, the substitution between phenylalanine and valine, the substitution between leucine and isoleucine and alanine, and the substitution between glycine and alanine.

The protein used in the present disclosure may also be a fusion protein linked to a heterologous portion through a peptide bond. Such a heterologous portion includes, for example, peptide components that make purification of a target protein easy (e.g., tag portions such as histidine tag, Strep-tag II; glutathione-S-transferase, maltose binding protein, and proteins such as mutants thereof utilized for the purification of the target protein), peptide components that enhance solubility of the target protein (e.g., Nus-tag), peptide components that work as a chaperon (e.g., trigger factor), peptide components having another function (e.g., a full length protein or parts thereof), and linkers.

The amino group-containing compound that can be used for the method of the present disclosure may be either an organic compound containing an amino group where a nitrogen atom is bonded to one or two hydrogen atoms or an organic compound containing an amino group where a nitrogen atom is not bonded to a hydrogen atom. In light of substrate specificity of the enzyme, a compound containing an amino group where a nitrogen atom is bonded to one or two hydrogen atoms is preferable, and a compound containing an amino group where a nitrogen atom is bonded to two hydrogen atoms is more preferable as the amino group-containing compound.

The amino group-containing compound that can be used for the method of the present disclosure is preferably a compound containing an amino group having an anionic group. The anionic group includes, for example, carboxyl group, sulfonate group, sulfate group and phosphate group.

The compound containing an amino group having a carboxyl group as the anionic group includes, for example, amino acids and peptides.

Amino acids include, for example, α-amino acids, β-amino acids, and γ-amino acids. α-Amino acids include, for example, glycine, alanine, valine, leucine, isoleucine, proline, methionine, phenylalanine, tryptophan, serine, threonine, asparagine, glutamine, tyrosine, cysteine, aspartic acid, glutamic acid, histidine, lysine and arginine. β-Amino acids include for example, β-alanine. γ-amino acids include for example, γ-butyric acid. The amino group in the amino acid may be any of an amino group where a nitrogen atom is bonded to two hydrogen atoms, an amino group where a nitrogen atom is bonded to one hydrogen atom, or an amino group where a nitrogen atom is not bonded to a hydrogen atom. Amino acids containing the amino group where a nitrogen atom is bonded to one hydrogen atom include, for example, sarcosine, N-methyl-β-alanine, N-methyltaurine, and proline. The amino acid may be either L-amino acids or D-amino acids.

A peptide is a compound having a structure where the amino acids described above are linked via an amide bond. The peptide includes, for example, oligopeptides having a structure where 2 to 10 amino acids are linked via an amide bond (e.g., dipeptide, tripeptide, tetrapeptide, pentapeptide, hexapeptide, heptapeptide, octapeptide), and polypeptides (proteins) having a structure where 11 or more amino acids are linked via an amide bond. The dipeptide includes, for example, aspartylphenylalanine, glycylglycine, and β-alanylhistidine, alanylglutamine.

The compound containing an amino group having a sulfonate group as the anionic group includes, for example, taurine, N-methyltaurine, and cysteic acid.

The compound containing an amino group having a sulfate group as the anionic group includes, for example, O-sulfoserine, and O-sulfothreonine.

The compound containing an amino group having a phosphate group as the anionic group includes, for example, ethanolamine phosphate, phosphoserine, and phosphothreonine.

The compound containing a carboxyl group that can be used for the method of the present disclosure is a compound containing an unsubstituted carboxyl group (e.g., free type, ion, salt). The compound containing a carboxyl group includes, for example, fatty acids, aromatic carboxylic acids and indolecarboxylic acids.

The fatty acids may be, for example, fatty acids having 6 to 18 carbon atoms, preferably fatty acids having 6 to 16 carbon atoms, more preferably fatty acids having 6 to 14 carbon atoms, and still more preferably fatty acids having 6 to 12 carbon atoms. The fatty acids having 6 to 18 carbon atoms include, for example, caproic acid (C6), enanthic acid (C7), caprylic acid (C8), pelargonic acid (C9), capric acid (C10), undecylic acid (C11), lauric acid (C12), tridecylic acid (C13), myristic acid (C14), pentadecylic acid (C15), palmitic acid, palmitoleic acid, sapienic acid (C16), margaric acid (C17), stearic acid, α-linolenic acid, γ-linolenic acid, linoleic acid, vaccenic acid, and oleic acid (C18) (the number in parenthesis denotes the number of carbon atoms). In addition thereto, mixed fatty acids such as palm coconut oil fatty acids, palm fatty acids, and hardened beef tallow fatty acids can be used.

The fatty acid is preferably a saturated fatty acid. Of the above fatty acids, the saturated fatty acids include caproic acid, enanthic acid, caprylic acid, pelargonic acid, capric acid, undecylic acid, lauric acid, tridecylic acid, myristic acid, pentadecylic acid, palmitic acid, margaric acid, and stearic acid.

The aromatic carboxylic acids include benzoic acid, phthalic acid, isophthalic acid, terephthalic acid, salicylic acid, gallic acid, and cinnamic acid.

The compound containing an N-acyl-amino group produced by the method of the present disclosure is a compound having a structure where an amino group of the above compound containing an amino group and a compound containing a carboxyl group of the above compound containing a carboxyl group have formed an amide bond. The above compound containing an N-acyl-amino group is produced by a reaction of the above compound containing an amino group and the above compound containing a carboxyl group in the presence of the above enzyme. A position of the amino group that reacts with the carboxylic group may be any position, for example, any of position α, position β, position γ, position δ, and position ε.

As the enzyme used for the method of the present disclosure, natural proteins or recombinant proteins can be utilized. The recombinant proteins can be obtained by using a cell free system vector or from a microorganism that produces the enzyme used in the present disclosure. The enzyme used in the present disclosure can be utilized as an unpurified enzyme, a crudely purified enzyme or a purified enzyme. These enzymes may be utilized as an immobilized enzyme fixed to a solid phase in a reaction.

The target enzyme is obtained by isolating the enzyme used for the method of the present disclosure by a known method and further purifying the enzyme as needed. The microorganism that produces the enzyme is preferably a transformed microorganism in light of obtaining the enzyme in a large amount. In the present disclosure, the term "transformation" intends not only introduction of a polynucleotide into a host cell but also modification of genome in the host cell.

A culture condition for a transformed microorganism is not particularly limited, and a standard cell culture condition can be used depending on a host cell. Media for culturing a transformed microorganism is known publicly, and for example, nutrient media such as LB media, and minimum media such as M9 media to which a carbon source, a nitrogen source, vitamin sources and the like are added can be used.

A culture temperature is 4 to 40° C., or 10 to 37° C. A culture time period is preferably 5 to 168 hours, or 8 to 72 hours. As a gas composition, a $CO_2$ concentration is about 6% to about 84%, and a pH value is about 5 to 9. It is also preferred to culture under an aerobic, anoxic or anaerobic condition depending on nature of a host cell.

Any suitable methods can be used as the culture method. Depending on a host cell, both shaking culture and static culture are possible, and if necessary, stirring may be performed and ventilation may be performed. Such a culture method includes, for example, a batch culture method, a fed-batch culture, and a continuous culture method. When expression of a certain protein produced by a transformed microorganism is under the control of an inducible promoter such as a lac promoter, an inducer such as IPTG (isopropyl-β-thiogalactopyranoside) may be added to induce the expression of the protein.

A produced target enzyme can be isolated and purified from an extract of a transformed microorganism by known salting-out, a precipitation method such as an isoelectric point precipitation method or a solvent precipitation method, a method utilizing molecular weight difference such as dialysis, ultrafiltration or gel filtration, a method utilizing specific affinity such as ion exchange chromatography, a method utilizing difference of hydrophobicity such as hydrophobic chromatography or reverse phase chromatography, and other affinity chromatography, SDS polyacrylamide electrophoresis, isoelectric point electrophoresis, or a combination thereof. When the target enzyme is expressed and secreted, a culture supernatant containing the target enzyme is obtained by removing microbial cells by centrifugation from the culture medium obtained by culturing the transformed microorganism. The target enzyme can also be isolated and purified from this culture supernatant.

A reaction in the presence of the above enzyme may be performed using a transformed microorganism that produces said enzyme or a treated product thereof (e.g., disrupted microorganism, lysed microorganism, lyophilized microorganism).

Preferably, a polynucleotide encoding the above enzyme used in the present disclosure may be a polynucleotide selected from among the following (a) to (d):

(a) a polynucleotide including a nucleotide sequence selected from among SEQ ID NOs: 12 to 22;
(b) a polynucleotide that hybridizes with a polynucleotide formed of a nucleotide sequence complementary to the nucleotide sequence selected from among SEQ ID NOs: 12 to 22 under a stringent condition, and encodes a protein having an N-acylase activity;
(c) a polynucleotide including a nucleotide sequence having 90% or more identity to the nucleotide sequence selected from among SEQ ID NOs: 12 to 22, and encodes a protein having an N-acylase activity; and
(d) a degenerate mutant of the polynucleotide selected from among (a) to (c).

The above polynucleotide may be DNA or RNA, but is preferably DNA. The nucleotide sequences of SEQ ID NOs: 12 to 22 encode amino acid sequences of SEQ ID NOs: 1 to 11, respectively.

In the above polynucleotide (b), the term "stringent condition" refers to a condition where a so-called specific hybrid is formed and a non-specific hybrid is not formed. For example, the stringent condition includes hybridization at about 45° C. in 6×SSC (sodium chloride/sodium citrate) followed by washing once or twice or more at 50 to 56° C. in 0.2×SSC and 0.1% SDS.

In the above polynucleotide (c), the identity of the nucleotide sequence to the nucleotide sequence of SEQ ID NOs: 12 to 22 may be 90% or more, 91% or more, 92% or more, 93% or more, 94% or more, 95% or more, 96% or more, 97% or more, 98% or more, or 99% or more.

In the above polynucleotide (d), the term "degenerate mutant" refers to a polynucleotide mutant in which at least one codon encoding a given amino acid residue in a polynucleotide before mutation has been changed to another codon encoding the same amino acid residue. Such a degenerate mutant is a mutant based on a silent mutation, and thus a protein (enzyme) encoded by the degenerate mutant is the same as a protein (enzyme) encoded by the polynucleotide before the mutation.

Preferably, the degenerate mutant is a polynucleotide mutant in which codons are changed to adapt to a codon usage in a host cell to which it is to be introduced. When a certain gene is expressed in a heterogeneous host cell (e.g., microorganism), due to difference in codon usage, corresponding tRNA molecular species is sometimes not sufficiently supplied to result in a reduced translation efficiency and/or incorrect translation (e.g., termination of translation). For example, low frequency codons shown in Table 1 are known in *Escherichia coli*.

TABLE 1

Low frequency codons in *Escherichia coli*

| Amino acid residue | Codon | Low frequency codon |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Therefore, in the present disclosure, it is possible to use a degenerate mutant that adapts to a codon usage in a host cell as described later. For example, the degenerate mutants may be those in which a codon(s) encoding one or more amino acid residues selected from among an arginine residue, a glycine residue, an isoleucine residue, a leucine residue, and a proline residue, has been changed. More specifically, the degenerate mutants may be those in which one or more codons selected from among low frequency codons (e.g., AGG, AGA, CGG, CGA, GGA, AUA, CUA and CCC) have been changed. Preferably, the degenerate mutant may include changes of one or more (e.g., one, two, three, four or five) codons selected from among the following:

i) change of at least one codon selected from among four codons encoding Arg (AGG, AGA, CGG and CGA) to another codon that encodes Arg (CGU or CGC);

ii) change of one codon encoding Gly (GGA) to another codon encoding Gly (GGG, GGU or GGC);

iii) change of one codon encoding Ile (AUA) to another codon encoding Ile (AUU or AUC);

(iv) change of one codon encoding Leu (CUA) to another codon encoding Leu (UUG, UUA, CUG, CUU or CUC); and (v) change of one codon encoding Pro (CCC) to another codon encoding Pro (CCG, CCA or CCU).

When the degenerate mutant is RNA, a nucleotide residue “U” should be used as described above, and when the degenerate mutant is DNA, “T” in place of the nucleotide residue “U” should be used. The number of mutations of nucleotide residues for adapting to the codon usage in the host cell is not particularly limited as long as the nucleotide residues encode the same protein before and after the mutation, and for example is 1 to 400, 1 to 300, 1 to 200, or 1 to 100.

A low frequency codon can easily be identified based on a type of any host cell and genome sequence information by utilizing technology known in the art. Therefore, the degenerate mutant may include the change of a low frequency codon to a non-low frequency codon (e.g., high frequency codon). Methods of designing mutants by taking account of not only the low frequency codons but also factors such as compatibility to a genomic GC content of a production bacterium strain are known (Alan Villalobos et al., Gene Designer: a synthetic biology tool for constructing artificial DNA segments, BMC Bioinformatics. 2006 Jun. 6; 7:285). Thus, such methods may be utilized. In this way, the mutants described above can appropriately be made depending on a type of any host cell (e.g., a microorganism as described later) into which it can be introduced.

A transformed microorganism having an enhanced activity of the above enzyme compared to a wild type microorganism is a microorganism including an expression unit containing a polynucleotide encoding the above enzyme and a promoter operably linked thereto.

In the present disclosure, the term “expression unit” refers to a minimum unit including a given polynucleotide to be expressed as a protein and a promoter operably linked thereto and enabling transcription of the polynucleotide and further production of the protein encoded by the polynucleotide. The expression unit may further include elements such as a terminator, a ribosome binding site, and a drug resistant gene. The expression unit may be DNA or RNA, but is preferably DNA. The expression unit may be homologous (i.e., inherent) or heterologous (i.e., non-inherent) to a host cell. The expression unit may also be an expression unit including one polynucleotide to be expressed as a protein and a promoter operably linked thereto (i.e., an expression unit enabling expression of monocistronic mRNA) or an expression unit including a plurality of polynucleotides (e.g., 2 or more, 3 or more, 4 or more, 5 or more, or 10 or more polynucleotides) and promoters operably linked thereto (i.e., an expression unit enabling expression of polycistronic mRNA). The expression unit can be included in a genomic region (e.g., a natural genomic region that is a natural locus in which the polynucleotide encoding the above protein inherently occurs or a non-natural genomic region that is not the natural locus) or a non-genomic region (e.g., intracellularly) in a microorganism (host cell). The expression units may be included at one or two or more (e.g., 1, 2, 3, 4 or 5) different positions in the genomic region. Specific forms of the expression unit included in the non-genomic region include, for example, plasmids, viral vectors, phages, and artificial chromosomes.

A promoter that configures the expression unit is not particularly limited as long as it can allow expression of a protein encoded by a polynucleotide linked downstream thereto in a host cell. For example, the promoter may be homologous or heterologous to the host cell. For example, constitutive or inducible promoters commonly used for the production of recombinant proteins can be used. Such a promoter includes, for example, PhoA promoter, PhoC promoter, T7 promoter, T5 promoter, T3 promoter, lac promoter, trp promoter, trc promoter, tac promoter, PR promoter, PL promoter, SP6 promoter, arabinose inducible promoter, cold shock promoter, and tetracycline inducible promoter. Preferably, a promoter having a potent transcription activity in a host cell can be used. The promoter having the potent transcription activity in the host cell includes, for example, promoters of genes highly expressed in host cells and promoters from viruses.

In one embodiment, a transformed microorganism having an enhanced activity of the above enzyme compared to a wild type microorganism may be (i) a microorganism including a heterologous expression unit containing a polynucleotide encoding the above enzyme and a promoter operably linked thereto. The term "heterologous expression unit" means that the expression unit is heterologous to a host cell. Therefore, in the present disclosure, at least one element that configures the expression unit is heterologous to the host cell. The element that is heterologous to the host cell and configures the expression unit includes, for example, the elements described above. Preferably, any one or both of the polynucleotide encoding the target enzyme and the promoter that configure the heterologous expression unit are heterologous to the host cell. Therefore, in the present disclosure, one or both of the polynucleotide encoding the target enzyme or the promoter are derived from an organism other than the host cell (e.g., a prokaryote and eukaryote, or a microorganism, an insect, a plant, and an animal such as a mammalian animal) or a virus, or synthesized artificially. A heterologous expression unit where at least one element that configures the expression unit is heterologous to the host cell is preferred as the heterologous expression unit.

In the microorganism of (i), a protein that constitutes the expression unit may be heterologous to the host cell. Such a microorganism includes, for example, a microorganism including an expression unit containing a polynucleotide encoding any of the following (A") to (C")

(A") a protein including an amino acid sequence selected from among SEQ ID NOs: 1 to 11;

(B") a protein including an amino acid sequence containing one or several amino acid substitutions, deletions, insertions or additions in the amino acid sequence selected from among SEQ ID NOs: 1 to 11, and having an N-acylase activity; or (C") a protein including an amino acid sequence 90% or more identity to the amino acid sequence selected from among SEQ ID NOs: 1 to 11, and having an N-acylase activity, and a promoter operably linked thereto.

In another embodiment, a transformed microorganism having an enhanced activity of the above enzyme compared to a wild type microorganism may be (ii) a microorganism including the expression unit containing a polynucleotide encoding the above enzyme and a promoter operably linked thereto in a non-natural genomic region or a non-genomic region.

In still another embodiment, a transformed microorganism having an enhanced activity of the above enzyme compared to a wild type microorganism may be (iii) a microorganism including the polynucleotides encoding the above enzyme in a plurality of copies in the expression unit. A plurality of copies may be a copy number that is, for example, 2 or more, 3 or more, 4 or more, 5 or more, or 10 or more.

In still another embodiment, a transformed microorganism having an enhanced activity of the above enzyme compared to a wild type microorganism may be (iv) a microorganism including a non-natural expression unit having a mutation introduced in an inherent expression unit (e.g., a promoter region) so that expression of the above enzyme is enhanced, or (v) a microorganism including a non-natural expression unit where a mutation has been introduced to the polynucleotide encoding the above enzyme by a technique such as genome editing so that the activity of the above enzyme is enhanced.

Preferably, the transformed microorganism having the enhanced activity of the above enzyme compared to the wild type microorganism is any microorganism of (i) to (iii).

In the present disclosure, host cells used as the transformed microorganism include, for example, bacteria such as bacteria belonging to Enterobacteriaceae, and fungi. The bacteria may be gram positive bacteria or gram negative bacteria. The gram positive bacteria include, for example, bacteria in the genera *Bacillus* and *Corynebacterium*. *Bacillus subtilis* is preferred as the bacterium in the genus *Bacillus*. *Corynebacterium glutamicum* is preferred as the bacterium in the genus *Corynebacterium*. The gram negative bacteria include, for example, bacteria in genera *Escherichia* and *Pantoea*. *Escherichia coli* is preferred as the bacterium in the genus *Escherichia*. *Pantoea ananatis* is preferred as the bacterium in the genus *Pantoea*. Microorganisms in genera *Saccharomyces* and *Schizosaccharomyces* are preferred as fungi. *Saccharomyces cerevisiae* is preferred as the microorganism in the genus *Saccharomyces*. *Schizosaccharomyces pombe* is preferred as the microorganism in the genus *Schizosaccharomyces*.

A host cell used as a transformed microorganism in the present disclosure may be, for example, a host having a weakened or deficient degradation system of an acylamino acids, fatty acids or amino acids. The host having the weakened or deficient degradation system includes, for example, a host having weakened or deficient protein such as an enzyme related to the above degradation system and a host producing an inhibiting factor of a protein such as an enzyme related to the above degradation system. The host having weakened or deficient protein such as the enzyme related to the above degradation system includes, for example, a host including a mutation that lowers or deletes an expression amount of the above protein in host genome and a host including a mutation that lowers or deletes an activity of the above protein in the host genome. The host producing or enhancing the inhibiting factor of the protein such as the enzyme related to the above degradation system includes, for example, a host having an expression unit of the above inhibiting factor introduced by transformation, a host including a mutation that enhances the expression amount of the above inhibiting factor in the host genome, and a host including a mutation that enhances the activity of the above inhibiting factor in the host genome. The protein such as the enzyme related to the degradation system of the acylamino acid includes acylase, and the protein such as the enzyme related to the degradation system of the fatty acid includes acyl CoA synthetase.

A host cell used as a transformed microorganism in the present disclosure may be, for example, a host where an uptake capacity of amino acids and fatty acids is enhanced to enhance supply efficiency of a substrate in an enzyme reaction to enhance production efficiency. The host where the above uptake capacity is enhanced includes, for example, a host producing or enhancing a protein such as an enzyme related to the above uptake capacity. The host producing or enhancing the protein such as the enzyme related to the above uptake capacity includes, for example, a host having an expression unit of the above protein introduced by transformation, a host including a mutation that enhances an expression amount of the above protein in the host genome, and a host having a mutation that enhances an activity of the above protein in the host genome.

The transformed microorganism used in the present disclosure can be made by any method known in the art. For example, the transformed microorganism as described above can be made by a method using an expression vector (e.g., a competent cell method, an electroporation method) or genome modification technology. When the expression vector is an integrative vector that produces homologous recombination with genomic DNA of a host cell, an expression unit can be integrated into the genomic DNA of the host cell by transformation. On the other hand, when the expression vector is a non-integrative vector that does not produce homologous recombination with genomic DNA of a host cell, the expression unit is not integrated into the genomic DNA of the host cell by transformation, can remain as a state of the expression vector and exist independently from the genomic DNA. Alternatively, according to genome-editing technology (e.g., CRISPR/Cas System, Transcription Activator-Like Effector Nucleases (TALEN)), it is possible to integrate the expression unit into the genomic DNA of the host cell and modify the expression unit inherently possessed by the host cell.

An expression vector may further include elements such as a terminator, a ribosome binding site and a drug resistant gene that function in a host cell as an expression unit, in addition to the minimum unit described above as the expression unit. The drug resistant genes include, for example, genes resistant to drugs such as tetracycline, ampicillin, kanamycin, hygromycin, and phosphinothricin.

An expression vector may also further include a region capable of homologous recombination with genome DNA of a host cell for the homologous recombination with the genome DNA of the host cell. For example, the expression vector may be designed so that an expression unit contained therein is located between a pair of homologous regions (e.g., homologous homology arm, loxP, FRT to a certain sequence in the genome of the host cell). A genomic region (target of a homologous region) of a host cell to which an expression unit is to be introduced is not particularly limited, and may be a locus of a gene expressed in large amount in the host cell.

An expression vector may be a plasmid, a viral vector, a phage, or an artificial chromosome. The expression vector may also be an integrative vector or a non-integrative vector. The integrative vector may be a vector that is entirely integrated into the genome of the host cell. Alternatively, the integrative vector may be a vector, only a part (e.g., an expression unit) of which is integrated into the genome of the host cell. The expression vector may further be a DNA vector or an RNA vector (e.g., a retrovirus vector). The expression vector may also be a commonly used expression vector. Such an expression vector includes, for example, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30), pET (e.g., pET28a) and derivatives thereof.

The compound containing an amino group and the compound containing a carboxyl group that are substrates used for the method of the present disclosure can be added to a reaction system including the above enzyme (e.g., an aqueous solution including the above enzyme, culture medium including a transformed microorganism which produces the above enzyme, a treated product of the microorganism which produces the above enzyme). Alternatively, the compound containing an amino group and the compound containing a carboxyl group produced in another reaction system can also be used as the substrates in the present disclosure.

When the method of the present disclosure is performed using the above enzyme itself (e.g., purified enzyme), an aqueous solution containing the above enzyme can be used as a reaction system. Buffer is preferred as the aqueous solution. The buffer includes, for example, phosphate buffer, Tris buffer, carbonate buffer, acetate buffer, and citrate buffer. A pH value is preferably, for example, about 5 to 10.

Amounts of the enzyme, the compound containing an amino group, and the compound containing a carboxyl group (substrates), as well as a reaction time period in the reaction system, can be appropriately controlled depending on an amount of a compound containing an N-acyl-amino group to be produced. A reaction temperature is not particularly limited as long as the reaction progresses, and is preferably 20 to 40° C.

The method of the present disclosure may be performed in combination with an ATP regenerating system. When the method of the present disclosure is performed using the above enzyme itself (e.g., purified enzyme), the combination with the ATP regenerating system includes, for example, a reaction by the combination (e.g., mixture) with an ATP regenerating enzyme. The ATP regenerating enzyme includes, for example, polyphosphate kinase, a combination of polyphosphoric acid:AMP phosphate transferase with polyphosphate kinase, and a combination of polyphosphoric acid:AMP phosphate transferase with adenylate kinase. When the method of the present disclosure is performed using a transformed microorganism which produces that enzyme or a treated product thereof, the combination with the ATP regenerating system includes, for example, using a microorganism having enhanced ATP supply capacity as a host. The microorganism having the enhanced ATP supply capacity includes, for example, a microorganism producing or enhancing the ATP regenerating enzyme described above. The microorganism producing or enhancing the ATP regenerating enzyme includes, for example, a host to which an expression unit of the ATP regenerating enzyme is introduced by transformation, a host including a mutation that enhances an expression amount of the ATP regenerating enzyme in the host genome, and a host including a mutation that enhances an activity of the ATP regenerating enzyme in the host genome.

Production of the compound containing an N-acyl-amino group can appropriately be confirmed. For example, such confirmation can be performed by adding a reaction stop solution (e.g., 1% (v/v) phosphoric acid, 75% (v/v) methanol aqueous solution) to the reaction system and filtrating the mixture through a filter followed by analyzing by UPLC-MS analysis.

EXAMPLES

Next, the present disclosure is described in more detail with reference to Examples, but the present disclosure is not limited to the following Examples.

Example 1: Expression and Purification of Acylamino Acid Synthetase (1) Construction of Acylamino Acid Synthetase-Expressing Plasmid For genes of Jasmonic acid-amido synthetase JAR1 from *Arabidopsis thaliana* (AtJAR1, Q9SKE2, SEQ ID NO:3), indole-3-acetic acid-amido synthetase GH3.6 from *Arabidopsis thaliana* (AtGH3-6, Q9LSQ4, SEQ ID NO:1), indole-3-acetic acid-amido synthetase GH3.5 from *Arabidopsis thaliana* (AtGH3-5, 081829, SEQ ID NO:4), GH3-10 from *Arabidopsis thaliana* (AtGH3-10, OAO98077, SEQ ID NO:5), 4-substituted benzoates-glutamate ligase GH3.12 from *Arabidopsis thaliana* (AtGH3-12, Q9LYU4, SEQ ID NO:6), indole-3-acetic acid-amido synthetase GH3.17 from *Arabidopsis thaliana* (AtGH3-17, Q9FZ87, SEQ ID NO:7), hypothetical protein from *Cystobacter fuscus* (CfHP, WP 002626336, SEQ ID NO:9), GH3 auxin-responsive promoter superfamily from *Synechococcus* sp. PCC 7335 (SsGH3, WP 006458022, SEQ ID NO:8), indoleacetate-lysine synthetase from *Pseudomonas savastanoi* (PsIAAL, P18204, SEQ ID NO:10), hypothetical protein from *Pantoea agglomerans* (PaHP, WP_031591948, SEQ ID NO:11), plasmid DNA where codons were optimized for expression in *E. coli* and the gene was inserted in NdeI and XhoI sites within a multicloning site of pET-28a(+) (Merck) were purchased from Eurofins Genomics K.K. The plasmids were designated as pET-28a-AtJAR1, pET-28a-AtGH3-6, pET-28a-AtGH3-5, pET-28a-AtGH3-10, pET-28a-AtGH3-12, pET-28a-AtGH3-17, pET-28a-CfHP, pET-28a-SsGH3, pET-28a-PsIAAL, and pET-28a-PaHP, respectively. A protein with fused His-tag and thrombin cleavage site on an N terminal side is expressed by this plasmid.

For the gene of probable indole-3-acetic acid-amido synthetase GH3.8 from *Oryza sativa* (OsGH3-8, A3BLSO, SEQ ID NO:2), synthesized DNA where codons were optimized for the expression in *E. coli* was purchased from GenScript. This synthesized DNA was treated with restriction enzymes NdeI and EcoRI, and ligated to pET28a(+) (Merck) similarly treated with NdeI and EcoRI. *E coli* JM109 strain was transformed with this ligated solution, and a target plasmid was extracted from kanamycin resistant strains and designated as pET-28a-OsGH3-8. A protein with fused His-tag and thrombin cleavage site on the N terminal side is expressed by this plasmid.

(2) Expression of Acylamino Acid Synthetase

The plasmids pET-28a-AtJAR1, pET-28a-AtGH3-6, pET-28a-OsGH3-8, pET-28a-AtGH3-5, pET-28a-AtGH3-12, pET-28a-AtGH3-17, pET-28a-PsIAAL, and pET-28a-PaHP were introduced into *E coli* BL21(DE3), respectively, and a transformant was inoculated to 100 mL of LB containing 25 mg/L of kanamycin and cultured with shaking at 37° C. using a Sakaguchi flask. When OD610 reached 0.6, 1 mM IPTG was added, and culturing with shaking was performed at 15° C. for 24 hours.

The plasmid pET-28a-CfHP was introduced into *E coli* BL21(DE3), and a transformant was inoculated to 100 mL of LB containing 25 mg/L of kanamycin and cultured with shaking at 37° C. using a Sakaguchi flask. When OD610 reached 0.2, 1 mM IPTG was added, and culturing with shaking was performed at 15° C. for 24 hours.

The plasmid pET-28a-AtGH3-10 was introduced into *E coli* BL21(DE3), and a transformant was inoculated to 100 mL of TB containing 25 mg/L of kanamycin and cultured with shaking at 37° C. using a Sakaguchi flask. When OD610 reached 0.4, 1 mM IPTG was added, and culturing with shaking was performed at 15° C. for 24 hours.

The plasmid pET-28a-SsGH3 was introduced into *E coli* BL21(DE3), and a transformant was inoculated to 100 mL of TB containing 25 mg/L of kanamycin and cultured with shaking at 37° C. using a Sakaguchi flask. When OD610 reached 0.2, 1 mM IPTG was added, and culturing with shaking was performed at 15° C. for 24 hours.

(3) Purification of Acylamino Acid Synthetase

After completion of the culture, microbial cells were collected from the obtained culture medium by centrifugation, then washed with and suspended in 20 mM Tris-HCl (pH 8.0), 300 mM NaCl and 0 or 10 mM imidazole, followed by disruption with sonication. Cell debris was removed from the sonicated suspension by centrifugation, and the resulting supernatant was used as a soluble fraction. The obtained soluble fraction was applied to a His-tag protein purification column His TALON superflow 5 ml Cartridge (Clontech) equilibrated with 20 mM Tris-HCl (pH 8.0), 300 mM NaCl, and 0 or 100 mM imidazole to adsorb proteins to a carrier. The proteins not adsorbed to the carrier (non-adsorbed proteins) were washed out using 20 mM Tris-HCl (pH 8.0), 300 mM NaCl, and 0 or 100 mM imidazole. Subsequently, the adsorbed protein was eluted using 20 mM Tris-HCl (pH 8.0), 300 mM NaCl, and 150 mM imidazole at a flow rate of 5 mL/min. The obtained fractions were collected, and concentration and buffer exchange were carried out using 20 mM Tris-HCl (pH 8.0) and Amicon Ultra-15 10 kDa (Merck). If necessary, an amount of the culture medium was increased to perform the purification.

Example 2: Synthesis of N-Caprinoylamino Acid Using Acylamino Acid Synthetase 2.0 mL of a reaction solution containing 50 mM Tris-HCl, 5 mM amino acid, 5 mM sodium caprate, 10 mM ATP, 10 mM $MgCl_2$, 1 mM DTT, 50 μg of the purified enzyme, pH 8.0 was incubated at 25° C. for 24 hours. After completion of the reaction, 0.8 mL of a reaction stop solution (1% (v/v) phosphoric acid, 75% (v/v) methanol) was added, and the mixture was filtrated through a filter followed by being subjected to the UPLC-MS analysis to detect a signal of a molecular weight corresponding to an N-caprinoyl amino acid.

A UPLC-MS analysis condition is as follows.

Apparatus: ACQUITY UPLC (Waters)

Column: ACQUITY UPLC BEH C18 1.7 2.1×100 mm Column (Waters)

Mobile phase A: 0.1% formic acid

Mobile phase B: acetonitrile

Gradient

TABLE 2

| Gradient condition | | |
|---|---|---|
| Time (min) | A % | B % |
| 0.0 | 60 | 40 |
| 3.0 | 20 | 80 |
| 4.0 | 20 | 80 |
| 4.1 | 60 | 40 |
| 5.0 | 60 | 40 |

Flow rate: 0.6 mL/min

Injection amount: 2 μL

Column temperature: 40° C.

Ionization method: ESI-negative

As a result of the UPLC-MS analysis, the signal of the molecular weight corresponding to the N-caprinoyl amino acid was confirmed in the reaction solution combining the enzyme and the amino acid shown in Table 3 below.

TABLE 3

Confirmation of ability of each acylamino acid synthetase to synthesize N-caprinoylamino acid

| Amino acid | m/z [M − H]⁻ | AtGH3-6 | OsGH3-8 | AtJAR1 | AtGH3-5 | AtGH3-10 | AtGH3-12 |
|---|---|---|---|---|---|---|---|
| Gly | 228 | + | + | + | + | + | + |
| L-Ala | 242 | + | + | + | + | + | + |
| L-Val | 270 | + | + | + | + | + | + |
| L-Leu | 284 | + | + | + | + | + | + |
| L-Ile | 284 | + | + | + | + | + | + |
| L-Pro | 268 | + | + | + | + | + | + |
| L-Met | 302 | + | + | + | + | + | + |
| L-Phe | 318 | + | + | + | + | + | + |
| L-Trp | 357 | + | + | + | + | + | + |
| L-Ser | 258 | + | + | + | + | + | + |
| L-Thr | 272 | + | + | + | + | + | + |
| L-Asn | 285 | + | + | + | + | + | + |
| L-Gln | 299 | + | + | + | + | + | + |
| L-Tyr | 334 | + | + | + | + | + | + |
| L-Cys | 274 | + | + | − | + | − | + |
| L-Asp | 286 | + | + | + | + | + | + |
| L-Glu | 300 | + | + | + | + | − | + |
| L-His | 308 | + | + | + | + | + | + |
| L-Lys | 299 | + | + | − | + | + | + |
| L-Arg | 327 | + | + | + | + | + | + |
| β-Ala | 242 | + | + | + | + | + | + |
| GABA | 256 | + | + | + | + | + | + |

| Amino acid | m/z [M − H]⁻ | AtGH3-17 | CfHP | SsGH3 | PsIAAL | PaHP |
|---|---|---|---|---|---|---|
| Gly | 228 | + | + | + | + | + |
| L-Ala | 242 | + | + | + | + | + |
| L-Val | 270 | + | + | + | + | + |
| L-Leu | 284 | + | + | + | + | + |
| L-Ile | 284 | + | + | + | + | + |
| L-Pro | 268 | − | + | − | + | − |
| L-Met | 302 | + | + | + | + | + |
| L-Phe | 318 | + | + | − | + | + |
| L-Trp | 357 | + | + | − | + | + |
| L-Ser | 258 | + | + | + | + | + |
| L-Thr | 272 | + | + | − | + | + |
| L-Asn | 285 | + | + | − | + | + |
| L-Gln | 299 | + | + | − | + | + |
| L-Tyr | 334 | + | + | − | + | + |
| L-Cys | 274 | + | + | − | + | + |
| L-Asp | 286 | + | + | + | + | + |
| L-Glu | 300 | + | + | − | + | + |
| L-His | 308 | − | + | − | + | − |
| L-Lys | 299 | − | + | − | + | + |
| L-Arg | 327 | − | + | − | + | + |
| β-Ala | 242 | + | + | + | + | + |
| GABA | 256 | + | + | − | + | + |

+: Detected,
−: Not detected

Example 3: Synthesis of N-Caprinoyl-Amino Acid Derivative, N-Caprinoyl-D-Amino Acid and N-Caprinoyl-Peptide Using Acylamino Acid Synthetase 0.2 mL of a reaction solution containing 50 mM Tris-HCl, 5 mM amino acid derivative or D-amino acid or peptide, 5 mM sodium caprate, 10 mM ATP, 10 mM $MgCl_2$, 1 mM DTT, 50 μg/mL of the purified enzyme, pH 8.0 was incubated at 25° C. for 24 hours. After completion of the reaction, 0.8 mL of the reaction stop solution (1% (v/v) phosphoric acid, 75% (v/v) methanol) was added, and the mixture was filtrated through the filter followed by being subjected to the UPLC-MS analysis to detect a signal of a molecular weight corresponding to an N-caprinoyl-amino acid derivative, an N-caprinoyl-amino acid or an N-caprinoyl-peptide. A condition for the UPLC-MS analysis is as described in Example 2.

As a result of the UPLC-MS analysis, the signal of the molecular weight corresponding to the N-caprinoyl-amino acid derivative, or N-caprinoyl-amino acid, or N-caprinoyl-peptide was confirmed in the reaction solution containing the enzyme in combination with the amino acid derivative or the D-amino acid or the peptide shown in Table 4 below.

TABLE 4

Confirmation of ability of each acylamino acid synthetase to synthesize N-caprinoyl compound

| Amino acid derivative/ D-amino acid/peptide | m/z [M − H]⁻ | AtGH 3-6 | OsGH 3-8 | AtJAR1 | AtGH 3-5 | AtGH 3-10 | AtGH 3-12 |
|---|---|---|---|---|---|---|---|
| Sarcosine | 242 | + | + | + | + | − | + |
| Taurine | 278 | + | + | + | + | + | + |
| D-Asp | 286 | + | + | + | + | + | + |
| D-Glu | 300 | + | + | + | + | + | + |
| D-Ala | 242 | + | + | + | + | + | + |
| D-Ile | 284 | + | + | + | + | − | + |
| D-Lys | 299 | + | + | − | + | − | + |
| D-Cys | 274 | + | + | − | + | + | − |
| L-Asp-L-Phe | 433 | + | + | − | + | − | + |
| L-Gly-L-Gly | 285 | + | + | + | + | + | + |
| Carnosine | 379 | + | + | − | + | − | + |

| Amino acid derivative/ D-amino acid/peptide | m/z [M − H]⁻ | AtGH 3-17 | CfHP | SsGH3 | PsIAAL | PaHP |
|---|---|---|---|---|---|---|
| Sarcosine | 242 | − | + | − | + | − |
| Taurine | 278 | + | + | + | + | + |
| D-Asp | 286 | + | + | + | + | + |
| D-Glu | 300 | + | + | + | + | + |
| D-Ala | 242 | − | + | + | + | + |
| D-Ile | 284 | + | + | − | + | + |
| D-Lys | 299 | − | + | − | + | + |
| D-Cys | 274 | − | + | − | + | + |
| L-Asp-L-Phe | 433 | − | + | − | + | − |
| L-Gly-L-Gly | 285 | + | + | + | + | + |
| Carnosine | 379 | − | + | − | + | + |

+: Detected,
−: Not detected

Example 4: Synthesis of N-Lauroylamino Acid, N-Lauroylamino Acid Derivative Using Acylamino Acid Synthetase 0.2 mL of a reaction solution containing 50 mM Tris-HCl, 5 mM amino acid or D-amino acid derivative, 5 mM sodium laurate, 10 mM ATP, 10 mM $MgCl_2$, 1 mM DTT, 200 μg/mL of the purified enzyme, pH 8.0 was incubated at 25° C. for 24 hours. After completion of the reaction, 0.8 mL of the reaction stop solution (1% (v/v) phosphoric acid, 75% (v/v) methanol) was added, and the mixture was filtrated through the filter followed by being subjected to the UPLC-MS analysis to detect a signal of a molecular weight corresponding to an N-lauroyl-amino acid or an N-lauroyl-amino acid derivative. The condition for the UPLC-MS analysis is as described in Example 2.

As a result of the UPLC-MS analysis, the signal of the molecular weight corresponding to the N-lauroyl-amino acid or the N-lauroyl-amino acid derivative was confirmed in the reaction solution containing the enzyme in combination with the amino acid or the amino acid derivative shown in Table 5 below.

TABLE 5

Confirmation of ability of each acylamino acid synthetase to synthesize N-lauroyl amino acids

| Amino acid/ amino acid derivative | m/z [M − H]⁻ | AtGH3-6 | OsGH3-8 | AtGH3-5 | AtGH3-12 |
|---|---|---|---|---|---|
| Gly | 256 | + | + | + | − |
| L-Ala | 270 | + | + | + | − |
| L-Thr | 300 | + | + | + | + |
| L-Asp | 314 | + | + | + | + |
| L-Glu | 328 | + | + | + | − |
| L-Lys | 327 | + | + | + | + |
| L-Arg | 355 | + | + | + | − |
| β-Ala | 270 | + | + | + | − |
| Sarcosine | 270 | + | − | + | − |
| Taurine | 306 | + | + | + | + |

+: Detected,
−: Not detected

Example 5: Synthesis of N-Acylamino Acid Using Acylamino Acid Synthetase 0.1 mL of a reaction solution containing 50 mM Tris-HCl, 5 mM amino acid, 5 mM sodium fatty acid, 10 mM ATP, 10 mM $MgCl_2$, 1 mM DTT, 200 μg/mL of the purified enzyme, pH 8.0 was incubated at 25° C. for 24 hours. As amino acids, L-Asp was used in AtGH3-6, OsGH3-8, AtGH3-5, AtGH3-12, and Gly or L-Ala was used in CfHP. After completion of the reaction, 0.4 mL of the reaction stop solution (1% (v/v) phosphoric acid, 75% (v/v) methanol) was added, and the mixture was filtrated through the filter followed by being subjected to the UPLC-MS analysis to quantify the produced N-acylamino acid by detection at UV 210 nm. The condition for the UPLC-MS analysis is as descried in Example 2. As a result of the analysis, 3.9 mM of Nα-capryloyl-L-aspartic acid, 4.5 mM of Nα-caprinoyl-L-aspartic acid and 2.2 mM of Nα-lauroyl-L-aspartic acid were detected when AtGH3-6 was used; 4.3 mM of Nα-capryloyl-L-aspartic acid, 4.6 mM of Nα-caprinoyl-L-aspartic acid and 3.5 mM of Nα-lauroyl- L-aspartic acid were detected when OsGH3-8 was used; 4.1 mM of Nα-capryloyl-L-aspartic acid, 4.6 mM of Nα-caprinoyl-L-aspartic acid and 2.5 mM of Nα-lauroyl-L-aspartic acid were detected when AtGH3-5 was used; 1.6 mM of Nα-capryloyl-L-aspartic acid, 0.6 mM of Nα-caprinoyl-L-aspartic acid and 0.2 mM of Nα-lauroyl-L-aspartic acid were detected when AtGH3-12 was used; 4.5 mM of Nα-capryloylglycine, 4.6 mM of Nα-caprinoylglycine, 0.1 mM of Nα-lauroylglycine, 3.1 mM of Nα-capryloyl-L-alanine, 3.6 mM of Nα-caprinoyl-L-alanine and 0.4 mM of Nα-lauroyl-L-alanine were detected when CfHP was used.

Example 6: Synthesis of N-Acylamino Acids Using Acylamino Acid Synthetase 0.1 mL of a reaction solution containing 50 mM Tris-HCl, 5 mM amino acid, 5 mM sodium fatty acid (3 mM of sodium palmitate or sodium stearate), 10 mM ATP, 10 mM $MgCl_2$, 1 mM DTT, 200 μg/mL of the purified enzyme, pH 8.0 was shaken at 25° C. for 24 hours. When sodium palmitate or sodium stearate was used, methanol at a final concentration of 10% (v/v) was contained in the reaction solution. As the amino acid, L-Asp was used in AtGH3-6, OsGH3-8, AtGH3-5, AtGH3-12, L-Ile was used in AtJAR1, L-Ala was used in AtGH3-10, SsGH3, L-Glu was used in AtGH3-17, Gly was used in CfHP, L-Lys was used in PsIAAL, and L-Cys was used in PaHP. After completion of the reaction, 0.4 mL of the reaction stop solution (1% (v/v) phosphoric acid, 75% (v/v) methanol) was added, and the mixture was filtrated through the filter followed by being subjected to the UPLC-MS analysis to detect a signal of a molecular weight corresponding to the N-acylamino acid.

The condition for the UPLC-MS analysis is as follows.

Apparatus: ACQUITY UPLC (Waters)

Column: ACQUITY UPLC BEH C18 1.7 μm 2.1×100 mm Column (Waters), mobile phase A: 0.1% formic acid; mobile phase B: acetonitrile Gradient:

TABLE 6

| Gradient condition | | |
|---|---|---|
| Time (min) | A % | B % |
| 0.0 | 90 | 10 |
| 3.0 | 0 | 100 |
| 4.0 | 0 | 100 |
| 4.1 | 90 | 10 |
| 5.0 | 90 | 10 |

Flow rate: 0.6 mL/minute

Injection amount: 2 μL

Column temperature: 40° C.

Ionization method: ESI-negative

As a result of the UPLC-MS analysis, the signal of the molecular weight corresponding to the appropriate N-acylamino acid was confirmed in the reaction solution containing the enzyme in combination with sodium fatty acid shown in Table 7 below.

TABLE 7

Confirmation of ability of acylamino acid synthetase to synthesize N-acylamino acid

| | L-Asp | | | | | L-Ile | |
|---|---|---|---|---|---|---|---|
| Fatty acid | m/z [M − H]⁻ | AtGH3-6 | OsGH3-8 | AtGH3-5 | AtGH3-12 | m/z [M − H]⁻ | AtJAR1 |
| Caproic acid | 230 | + | + | + | + | 228 | + |
| Caprylic acid | 258 | + | + | + | + | 256 | + |
| Capric acid | 286 | + | + | + | + | 284 | + |
| Lauric acid | 314 | + | + | + | + | 312 | + |
| myristic acid | 342 | + | + | + | + | 340 | − |
| Palmitic acid | 370 | + | + | + | + | 368 | − |
| Linoleic acid | 394 | − | − | − | + | 392 | − |

| | L-Ala | | | L-Glu | | Gly | |
|---|---|---|---|---|---|---|---|
| Fatty acid | m/z [M − H]⁻ | AtGH3-10 | SsGH3 | m/z [M − H]⁻ | AtGH3-17 | m/z [M − H]⁻ | CfHP |
| Caproic acid | 186 | + | + | 244 | + | 172 | + |
| Caprylic acid | 214 | + | + | 272 | + | 200 | + |
| Capric acid | 242 | + | + | 300 | + | 228 | + |
| Lauric acid | 270 | + | + | 328 | + | 256 | + |
| myristic acid | 298 | + | + | 356 | + | 284 | + |
| Palmitic acid | 326 | − | − | 384 | + | 312 | + |
| Linoleic acid | 350 | − | − | 408 | − | 336 | − |

| | L-Lys | | L-Cys | |
|---|---|---|---|---|
| Fatty acid | m/z [M − H]⁻ | AtGH3-10 | m/z [M − H]⁻ | AtGH3-17 |
| Caproic acid | 243 | + | 218 | + |
| Caprylic acid | 271 | + | 246 | + |
| Capric acid | 299 | + | 274 | + |
| Lauric acid | 327 | + | 302 | + |
| myristic acid | 355 | + | 330 | − |
| Palmitic acid | 383 | + | 358 | − |
| Linoleic acid | 407 | − | 382 | − |

+: Detected,
−: Not detected

Example 7: Analysis of ATP Dependency of Acylamino Acid Synthetase 0.25 mL of a reaction solution containing 50 mM Tris-HCl, 5 mM amino acid, 5 mM sodium caprate, 10 mM or 0 mM ATP, 10 mM $MgCl_2$, 1 mM DTT, 50 μg of the purified enzyme, pH 8.0 was incubated at 25° C. for 24 hours. As the amino acid, L-Asp and Gly were used in AtGH3-6 and CfHP, respectively. After completion of the reaction, 0.8 mL of the reaction stop solution (1% (v/v) phosphoric acid, 75% (v/v) methanol) was added to 0.2 mL of the reaction solution, and the mixture was filtrated through the filter followed by being subjected to the UPLC-MS analysis to quantify a produced N-caprinoylamino acid by detection at UV 210 nm. The condition for the UPLC-MS analysis is as described in Example 2. As a result of the analysis, 3.8 mM and 5.2 mM of the N-caprinoylamino acids were detected in AtGH3-6 and CfHP, respectively in the presence of ATP. However, in the absence of ATP, no signal of the molecular weight corresponding to the N-caprinoylamino acid was detected when any of AtGH3-6 and CfHP was used.

Example 8: Synthesis of N-Capryloylamino Acid Using Microbial Cells Expressing Acylamino Acid Synthetase (1) Preparation of Various Microbial Cell Suspension BL21(DE3)/pET-28a-AtGH3-6, BL21(DE3)/pET-28a-OsGH3-8, BL21(DE3)/pET-28a-AtGH3-5, and BL21 (DE3)/pET-28a were inoculated to 100 mL of LB medium containing 25 mg/L of kanamycin in a Sakaguchi flask, respectively and cultured with shaking at 37° C. When OD610 reached 0.6, 1 mM IPTG was added, and culturing with shaking was continued at 15° C. for 24 hours.

BL21(DE3)/pET-28a-CfHP was inoculated to 100 mL of LB medium containing 25 mg/L of kanamycin in a Sakaguchi flask, and cultured with shaking at 37° C. When OD610 reached 0.2, 1 mM IPTG was added, and culturing with shaking was continued at 15° C. for 24 hours.

(Preparation of Cell Free Extract Solution)

After completion of the culture, microbial cells were collected from 5 mL of the resulting culture medium by centrifugation and washed with 20 mM Tris-HCl (pH 7.6) followed by being suspended in 1 mL of BugBuster (registered tradename) Master Mix (Merck). After being incubated at room temperature for 10 to 20 minutes, a supernatant was collected by centrifugation and used as a cell free extract solution.

(Preparation of Washed Microbial Cell Suspension)

After completion of the culture, microbial cells were collected from 5 mL of the resulting culture medium by centrifugation and washed with 20 mM Tris-HCl (pH 7.6) followed by being suspended in 1 mL of 20 mM Tris-HCl (pH 7.6) to use as a washed microbial cell suspension.

(Preparation of Microbial Cell Suspension)

After completion of the culture, 15 mL of the resulting culture medium was concentrated to 3 mL by centrifugation to use as a microbial cell suspension.

(2) Synthesis Reaction of N-Capryloylamino Acid Using Various Microbial Cell Suspension 0.3 mL of a reaction solution containing 33.3 mM Tris-HCl, 3.3 mM amino acid, 3.3 mM sodium caprylate, 6.7 mM or 0 mM ATP, 6.7 mM $MgCl_2$, 0.7 mM DTT, 30 μg of the microbial cell suspension (cell free extract solution, washed microbial suspension, microbial suspension), pH 8.0 was incubated at 25° C. for 24 hours. As the amino acid, L-Asp was used in AtGH3-6, OsGH3-8, AtGH3-5, and Gly or L-Ala was used in CfHP. After completion of the reaction, 0.8 mL of the reaction stop solution (1% (v/v) phosphoric acid, 75% (v/v) methanol) was added, and the mixture was filtrated through the filter followed by being subjected to the UPLC-MS analysis to detect a signal of a molecular weight corresponding to the N-capryloylamino acid. The condition for the UPLC-MS analysis is as described in Example 2. As a result of the UPLC-MS analysis, the signal of the molecular weight corresponding to the appropriate N-capryloylamino acid was confirmed in the reaction solution using the microbial cell suspension and the like shown in Table 8 below.

TABLE 8

Confirmation of N-acylamino acid synthetase prepared in various expression systems to synthesize N-acylamino acid.

| Strain | Amino acid | m/z $[M-H]^-$ | +ATP Cell free extract solution | +ATP Washed microbial cell suspension | +ATP Microbial cell suspension | −ATP Microbial cell suspension |
|---|---|---|---|---|---|---|
| BL21(DE3)/pET-28a-AtGH3-6 | L-Asp | 258 | + | + | + | + |
| BL21(DE3)/pET-28a-OsGH3-8 | | | + | + | + | + |
| BL21(DE3)/pET-28a-AtGH3-5 | | | + | + | + | + |
| BL21(DE3)/pET-28a | | | − | − | − | − |
| BL21(DE3)/pET-28a-CfHP | Gly | 200 | − | + | + | + |
| BL21(DE3)/pET-28a | | | − | − | − | − |
| BL21(DE3)/pET-28a-CfHP | L-Ala | 214 | − | + | + | + |
| BL21(DE3)/pET-28a | | | − | − | − | − |

+: Detected,

−: Not detected

In the reaction using the purified enzyme, the production of the N-acylamino acid was not observed in the absence of ATP (Example 7). In the reaction using the microbial cell suspension, however, the production of the N-acylamino acid was observed even in the absence of ATP. Thus, it is conceivable that the enzyme reaction progressed by utilizing ATP contained in the microbial cells.

As a result of quantifying the produced N-acylamino acid by detection at UV 210 nm, when Gly was used as the substrate in CfHP, 2.8 mM, 2.2 mM and 2.6 mM N-capryloylamino acids were detected in the washed microbial cell suspension, the microbial cell suspension (in the presence of ATP) and the microbial cell suspension (in the absence of ATP), respectively. When L-Ala was used as the substrate in CfHP, 2.4 mM, 0.9 mM and 1.0 mM N-capryloylamino acids were detected in the washed microbial cell suspension, the microbial cell suspension (in the presence of ATP) and the microbial cell suspension (in the absence of ATP), respectively.

INDUSTRIAL APPLICABILITY

The present disclosure is useful for the productionre of N-acyl-amino group-containing compounds available for materials for perfumery and cosmetics (e.g., surfactants).

SEQUENCE LISTING FREE TEXT

SEQ ID NOs: 1 to 11 represent amino acid sequences of AtGH3-6, OsGH3-8, AtJAR1(AtGH3-11), AtGH3-5, AtGH3-10, AtGH3-12, AtGH3-17, SsGH3, CfHP (WP_002626336), PsIAAL, and PaHP(WP_031591948), respectively.

SEQ ID NOs: 12 to 22 represent nucleotide sequences codon-optimized for the expression in *Escherichia coli* and encoding the amino acid sequences of SEQ ID NOs: 1 to 11, respectively.

The invention claimed is:

1. A method of producing a compound containing an N-acyl-amino group, the method comprising:

reacting a compound containing an amino group with a fatty acid in a culture medium comprising a microorganism, wherein the microorganism produces an enzyme, and said reacting results in production of the compound containing an N-acyl-amino group, wherein the fatty acid is a saturated fatty acid having 6 to 18 carbon atoms, and isolating the compound containing an N-acyl-amino group from the culture medium, wherein the enzyme has an ability to bond a carboxyl group and an amino group in an ATP dependent manner to form an amide bond, wherein the enzyme is selected from the group consisting of:

(A) a protein comprising an amino acid sequence selected from the group consisting of SEQ ID NOs: 1 to 9, (B) a protein comprising an amino acid sequence containing one to twenty amino acid substitutions, deletions, insertions, or additions in the amino acid sequence selected from the group consisting of SEQ ID NOs: 1 to 9, and said protein having an N-acylase activity, and (C) a protein comprising an amino acid sequence having 95% or more identity to the amino acid sequence selected from the group consisting of SEQ ID NOs: 1 to 9, and said protein having an N-acylase activity.

2. The method according to claim 1, wherein the enzyme is selected from the group consisting of:

(A) a protein comprising an amino acid sequence selected from the group consisting of SEQ ID NOs: 1 to 9;

(B) a protein comprising an amino acid sequence containing one to ten amino acid substitutions, deletions, insertions, or additions in the amino acid sequence selected from the group consisting of SEQ ID NOs: 1 to 9, and said protein having an N-acylase activity; and (C) a protein comprising an amino acid sequence having 98% or more identity to the amino acid sequence selected from the group consisting of SEQ ID NOs: 1 to 9, and said protein having an N-acylase activity.

3. The method according to claim 1, wherein the compound containing an amino group is a compound containing an amino group having an anionic group.

4. The method according to claim 1, wherein the compound containing an amino group is an amino acid or a peptide.

5. The method according to claim 4, wherein the compound containing an amino group is an α-amino acid, a β-amino acid, or a γ-amino acid, or a dipeptide thereof.

6. The method according to claim 4, wherein the amino acid is an L-amino acid or a D-amino acid.

7. The method according to claim 1, wherein the compound containing an amino group is selected from the group consisting of:

(1) an amino acid selected from the group consisting of:

(a) an α-amino acid selected from the group consisting of glycine, alanine, valine, leucine, isoleucine, proline, methionine, phenylalanine, tryptophan, serine, threonine, asparagine, glutamine, tyrosine, cysteine, aspartic acid, glutamic acid, histidine, lysine, and arginine;

(b) β-alanine;

(c) a γ-aminobutyric acid; and (d) sarcosine;

(2) taurine; and (3) a dipeptide selected from the group consisting of aspartylphenylalanine, glycylglycine, and alanylhistidine.

8. The method according to claim 1, wherein the fatty acid has 6 to 12 carbon atoms.

9. The method according to claim 1, wherein said microorganism is:

(i) a microorganism comprising a heterologous expression unit containing a polynucleotide encoding said enzyme and a promoter operably linked thereto;

(ii) a microorganism comprising an expression unit containing a polynucleotide encoding said enzyme and a promoter operably linked thereto in a non-natural genomic region or a non-genomic region; or (iii) a microorganism comprising a polynucleotide encoding said enzyme in multiple copy number in an expression unit.

10. The method according to claim 1, wherein said microorganism is a bacterium belonging to Enterobacteriaceae.

11. The method according to claim 10, wherein said bacterium is *Escherichia coli.*

12. A method of producing a compound containing an N-acyl-amino group, the method comprising:

reacting a compound containing an amino group with a fatty acid in a culture medium comprising a microorganism, wherein the microorganism produces an enzyme, and said reacting results in production of the compound containing an N-acyl-amino group, and isolating the compound containing an N-acyl-amino group from the culture medium, wherein the enzyme has an ability to bond a carboxyl group and an amino group in an ATP dependent manner to form an amide bond, wherein the enzyme is selected from the group consisting of:

(A) a protein comprising an amino acid sequence selected from the group consisting of SEQ ID NOs: 1 to 9, (B) a protein comprising an amino acid sequence containing one to twenty amino acid substitutions, deletions, insertions, or additions in the amino acid sequence selected from the group consisting of SEQ ID NOs: 1 to 9, and said protein having an N-acylase activity, and (C) a protein comprising an amino acid sequence having 95% or more identity to the amino acid sequence selected from the group consisting of SEQ ID NOs: 1 to 9, and said protein having an N-acylase activity;

wherein the fatty acid is selected from the group consisting of caproic acid (C6), enanthic acid (C7), caprylic acid (C8), pelargonic acid (C9), capric acid (C10), undecylic acid (C11), lauric acid (C12), tridecylic acid (C13), myristic acid (C14), pentadecylic acid (C15), palmitic acid, palmitoleic acid, sapienic acid (C16), margaric acid (C17), stearic acid, α-linolenic acid, γ-linolenic acid, linoleic acid, vaccenic acid, oleic acid (C18), coconut oil fatty acid, palm fatty acid, hardened beef tallow fatty acid, and combinations thereof.

13. The method of claim 1, wherein the fatty acid is selected from the group consisting of caproic acid (C6), caprylic acid (C8), capric acid (C10), lauric acid (C12), myristic acid (C14), palmitic acid, and combinations thereof.

14. The method of claim 1, wherein the fatty acid is selected from the group consisting of caproic acid (C6), caprylic acid (C8), capric acid (C10), lauric acid (C12), myristic acid (C14), palmitic acid, linoleic acid, and combinations thereof.

* * * * *

```
                      SEQUENCE LISTING


<160> NUMBER OF SEQ ID NOS: 22

<210> SEQ ID NO 1
<211> LENGTH: 612
<212> TYPE: PRT
<213> ORGANISM: Arabidopsis thaliana

<400> SEQUENCE: 1

Met Pro Glu Ala Pro Lys Ile Ala Ala Leu Glu Val Ser Asp Glu Ser
1               5                   10                  15

Leu Ala Glu Lys Asn Lys Asn Lys Leu Gln Phe Ile Glu Asp Val Thr
            20                  25                  30

Thr Asn Ala Asp Asp Val Gln Arg Arg Val Leu Glu Glu Ile Leu Ser
        35                  40                  45

Arg Asn Ala Asp Val Glu Tyr Leu Lys Arg His Gly Leu Glu Gly Arg
    50                  55                  60

Thr Asp Arg Glu Thr Phe Lys His Ile Met Pro Val Val Thr Tyr Glu
65                  70                  75                  80

Asp Ile Gln Pro Glu Ile Asn Arg Ile Ala Asn Gly Asp Lys Ser Gln
                85                  90                  95

Val Leu Cys Ser Asn Pro Ile Ser Glu Phe Leu Thr Ser Ser Gly Thr
            100                 105                 110

Ser Gly Gly Glu Arg Lys Leu Met Pro Thr Ile Glu Glu Glu Leu Asp
        115                 120                 125

Arg Arg Ser Leu Leu Tyr Ser Leu Leu Met Pro Val Met Asp Gln Phe
    130                 135                 140

Val Pro Gly Leu Asp Lys Gly Lys Gly Met Tyr Phe Leu Phe Ile Lys
145                 150                 155                 160

Ser Glu Ser Lys Thr Pro Gly Gly Leu Pro Ala Arg Pro Val Leu Thr
                165                 170                 175

Ser Tyr Tyr Lys Ser Ser His Phe Lys Asn Arg Pro Tyr Asp Pro Tyr
            180                 185                 190

Thr Asn Tyr Thr Ser Pro Asn Gln Thr Ile Leu Cys Ser Asp Ser Tyr
        195                 200                 205

Gln Ser Met Tyr Ser Gln Met Leu Cys Gly Leu Cys Gln His Lys Glu
    210                 215                 220

Val Leu Arg Val Gly Ala Val Phe Ala Ser Gly Phe Ile Arg Ala Ile
225                 230                 235                 240
```

```
Lys Phe Leu Glu Lys His Trp Pro Glu Leu Ala Arg Asp Ile Arg Thr
                245                 250                 255

Gly Thr Leu Ser Ser Glu Ile Thr Asp Ser Ser Val Arg Glu Ala Val
            260                 265                 270

Gly Glu Ile Leu Lys Pro Asp Pro Lys Leu Ala Asp Phe Val Glu Ser
        275                 280                 285

Glu Cys Arg Lys Thr Ser Trp Gln Gly Ile Ile Thr Arg Leu Trp Pro
    290                 295                 300

Asn Thr Lys Tyr Val Asp Val Ile Val Thr Gly Thr Met Ser Gln Tyr
305                 310                 315                 320

Ile Pro Thr Leu Asp Tyr Tyr Ser Asn Gly Leu Pro Leu Val Cys Thr
                325                 330                 335

Met Tyr Ala Ser Ser Glu Cys Tyr Phe Gly Val Asn Leu Arg Pro Leu
            340                 345                 350

Cys Lys Pro Ser Glu Val Ser Tyr Thr Leu Ile Pro Asn Met Ala Tyr
        355                 360                 365

Phe Glu Phe Leu Pro Val His Arg Asn Ser Gly Val Thr Ser Ser Ile
    370                 375                 380

Ser Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
                405                 410                 415

Tyr Ala Gly Leu Tyr Arg Tyr Arg Val Gly Asp Val Leu Ser Val Ala
            420                 425                 430

Gly Phe Lys Asn Asn Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
                485                 490                 495

Tyr Val Leu Phe Trp Glu Leu Cys Leu Asn Gly Asn Thr Pro Ile Pro
            500                 505                 510

Pro Ser Val Phe Glu Asp Cys Cys Leu Thr Ile Glu Glu Ser Leu Asn
        515                 520                 525

Ser Val Tyr Arg Gln Gly Arg Val Ser Asp Lys Ser Ile Gly Pro Leu
    530                 535                 540

Glu Ile Lys Met Val Glu Ser Gly Thr Phe Asp Lys Leu Met Asp Tyr
545                 550                 555                 560

Ala Ile Ser Leu Gly Ala Ser Ile Asn Gln Tyr Lys Thr Pro Arg Cys
                565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Ser Pro Gly His Lys Gln
        595                 600                 605

Trp Gly Ser Asn
    610
```

<210> SEQ ID NO 2
<211> LENGTH: 605
<212> TYPE: PRT
<213> ORGANISM: Oryza sativa

<400> SEQUENCE: 2

```
Met Ala Val Met Thr Asp Val Ser Thr Thr Gly Thr Ala Leu Arg Thr
1               5                   10                  15

Pro Ala Ala Gly Ala Val Lys Glu Gly Asp Val Glu Lys Leu Arg Phe
            20                  25                  30

Ile Asp Glu Met Thr Thr Asn Val Asp Ala Val Gln Glu Arg Val Leu
        35                  40                  45

Gly Glu Ile Leu Gly Arg Asn Ala Gly Thr Glu Tyr Leu Thr Lys Cys
    50                  55                  60

Gly Leu Asp Gly Ala Thr Asp Arg Ala Ala Phe Arg Ala Lys Val Pro
65                  70                  75                  80

Val Val Ser Tyr Asp Asp Leu Gln Pro Tyr Ile Gln Arg Ile Ala Asn
                85                  90                  95

Gly Asp Arg Ser Pro Ile Leu Ser Thr His Pro Val Ser Glu Phe Leu
            100                 105                 110

Thr Ser Ser Gly Thr Ser Ala Gly Glu Arg Lys Leu Met Pro Thr Ile
        115                 120                 125

Met Asp Glu Leu Asp Arg Arg Gln Leu Leu Tyr Ser Leu Leu Met Pro
    130                 135                 140

Val Met Asn Leu Tyr Val Pro Gly Leu Asp Lys Gly Lys Gly Leu Tyr
145                 150                 155                 160

Phe Leu Phe Val Lys Ser Glu Thr Lys Thr Pro Gly Gly Leu Thr Ala
                165                 170                 175

Arg Pro Val Leu Thr Ser Tyr Tyr Lys Ser Asp His Phe Lys Asn Arg
            180                 185                 190

Pro Tyr Asp Pro Tyr His Asn Tyr Thr Ser Pro Thr Ala Ala Ile Leu
        195                 200                 205

Cys Ala Asp Ala Phe Gln Ser Met Tyr Ala Gln Met Val Cys Gly Leu
    210                 215                 220

Cys Gln Arg Asn Asp Val Leu Arg Leu Gly Ala Val Phe Ala Ser Gly
225                 230                 235                 240

Leu Leu Arg Ala Ile Arg Phe Leu Gln Leu Asn Trp Glu Gln Leu Ala
                245                 250                 255

Asp Asp Ile Glu Ser Gly Glu Leu Thr Pro Arg Val Thr Asp Pro Ser
            260                 265                 270

Val Arg Glu Ala Val Ala Ala Ile Leu Leu Pro Asp Pro Glu Leu Ala
        275                 280                 285

Lys Leu Ile Arg Ala Glu Cys Ser Lys Gly Asp Trp Ala Gly Ile Ile
    290                 295                 300

Thr Arg Val Trp Pro Asn Thr Lys Tyr Leu Asp Val Ile Val Thr Gly
305                 310                 315                 320

Ala Met Ala Gln Tyr Ile Pro Thr Leu Glu Phe Tyr Ser Gly Gly Leu
                325                 330                 335

Pro Met Ala Cys Thr Met Tyr Ala Ser Ser Glu Cys Tyr Phe Gly Leu
            340                 345                 350

Asn Leu Arg Pro Met Cys Asp Pro Ser Glu Val Ser Tyr Thr Ile Met
        355                 360                 365

Pro Asn Met Gly Tyr Phe Glu Phe Leu Pro Val Asp Glu Thr Gly Ala
    370                 375                 380

Ala Ser Gly Asp Ala Thr Gln Leu Val Asp Leu Ala Arg Val Glu Val
385                 390                 395                 400

Gly Arg Glu Tyr Glu Leu Val Ile Thr Thr Tyr Ala Gly Leu Asn Arg
                405                 410                 415
```

```
Tyr Arg Val Gly Asp Val Leu Arg Val Thr Gly Phe His Asn Ala Ala
            420                 425                 430

Pro Gln Phe Arg Phe Val Arg Arg Lys Asn Val Leu Leu Ser Ile Glu
        435                 440                 445

Ser Asp Lys Thr Asp Glu Ala Glu Leu Gln Arg Ala Val Glu Arg Ala
    450                 455                 460

Ser Ala Leu Leu Arg Pro His Gly Ala Ser Val Val Glu Tyr Thr Ser
465                 470                 475                 480

Gln Ala Cys Thr Lys Arg Ile Pro Gly His Tyr Val Ile Tyr Trp Glu
                485                 490                 495

Leu Leu Thr Lys Gly Ala Gly Ala Thr Val Val Asp Ala Asp Thr Leu
            500                 505                 510

Gly Arg Cys Cys Leu Glu Met Glu Glu Ala Leu Asn Thr Val Tyr Arg
        515                 520                 525

Gln Ser Arg Val Ala Asp Gly Ser Ile Gly Pro Leu Glu Ile Arg Val
    530                 535                 540

Val Arg Pro Gly Thr Phe Glu Glu Leu Met Asp Tyr Ala Ile Ser Arg
545                 550                 555                 560

Gly Ala Ser Ile Asn Gln Tyr Lys Val Pro Arg Cys Val Thr Phe Pro
                565                 570                 575

Pro Ile Val Glu Leu Leu Asp Ser Arg Val Val Ser Ser His Phe Ser
            580                 585                 590

Pro Ala Leu Pro His Trp Thr Pro Ala Arg Arg Ser Glu
        595                 600                 605


<210> SEQ ID NO 3
<211> LENGTH: 575
<212> TYPE: PRT
<213> ORGANISM: Arabidopsis thaliana

<400> SEQUENCE: 3

Met Leu Glu Lys Val Glu Thr Phe Asp Met Asn Arg Val Ile Asp Glu
1               5                   10                  15

Phe Asp Glu Met Thr Arg Asn Ala His Gln Val Gln Lys Gln Thr Leu
            20                  25                  30

Lys Glu Ile Leu Leu Lys Asn Gln Ser Ala Ile Tyr Leu Gln Asn Cys
        35                  40                  45

Gly Leu Asn Gly Asn Ala Thr Asp Pro Glu Glu Ala Phe Lys Ser Met
    50                  55                  60

Val Pro Leu Val Thr Asp Val Glu Leu Glu Pro Tyr Ile Lys Arg Met
65                  70                  75                  80

Val Asp Gly Asp Thr Ser Pro Ile Leu Thr Gly His Pro Val Pro Ala
                85                  90                  95

Ile Ser Leu Ser Ser Gly Thr Ser Gln Gly Arg Pro Lys Phe Ile Pro
            100                 105                 110

Phe Thr Asp Glu Leu Met Glu Asn Thr Leu Gln Leu Phe Arg Thr Ala
        115                 120                 125

Phe Ala Phe Arg Asn Arg Asp Phe Pro Ile Asp Asp Asn Gly Lys Ala
    130                 135                 140

Leu Gln Phe Ile Phe Ser Ser Lys Gln Tyr Ile Ser Thr Gly Gly Val
145                 150                 155                 160

Pro Val Gly Thr Ala Thr Thr Asn Val Tyr Arg Asn Pro Asn Phe Lys
                165                 170                 175

Ala Gly Met Lys Ser Ile Thr Ser Pro Ser Cys Ser Pro Asp Glu Val
```

```
            180                 185                 190

Ile Phe Ser Pro Asp Val His Gln Ala Leu Tyr Cys His Leu Leu Ser
        195                 200                 205

Gly Ile Leu Phe Arg Asp Gln Val Gln Tyr Val Phe Ala Val Phe Ala
    210                 215                 220

His Gly Leu Val His Ala Phe Arg Thr Phe Glu Gln Val Trp Glu Glu
225                 230                 235                 240

Ile Val Thr Asp Ile Lys Asp Gly Val Leu Ser Asn Arg Ile Thr Val
                245                 250                 255

Pro Ser Val Arg Thr Ala Met Ser Lys Leu Leu Thr Pro Asn Pro Glu
            260                 265                 270

Leu Ala Glu Thr Ile Arg Thr Lys Cys Met Ser Leu Ser Asn Trp Tyr
        275                 280                 285

Gly Leu Ile Pro Ala Leu Phe Pro Asn Ala Lys Tyr Val Tyr Gly Ile
    290                 295                 300

Met Thr Gly Ser Met Glu Pro Tyr Val Pro Lys Leu Arg His Tyr Ala
305                 310                 315                 320

Gly Asp Leu Pro Leu Val Ser His Asp Tyr Gly Ser Ser Glu Gly Trp
                325                 330                 335

Ile Ala Ala Asn Val Thr Pro Arg Leu Ser Pro Glu Glu Ala Thr Phe
            340                 345                 350

Ala Val Ile Pro Asn Leu Gly Tyr Phe Glu Phe Leu Pro Val Ser Glu
        355                 360                 365

Thr Gly Glu Gly Glu Glu Lys Pro Val Gly Leu Thr Gln Val Lys Ile
    370                 375                 380

Gly Glu Glu Tyr Glu Val Val Ile Thr Asn Tyr Ala Gly Leu Tyr Arg
385                 390                 395                 400

Tyr Arg Leu Gly Asp Val Val Lys Val Ile Gly Phe Tyr Asn Asn Thr
                405                 410                 415

Pro Gln Leu Lys Phe Ile Cys Arg Arg Asn Leu Ile Leu Ser Ile Asn
            420                 425                 430

Ile Asp Lys Asn Thr Glu Arg Asp Leu Gln Leu Ser Val Glu Ser Ala
        435                 440                 445

Ala Lys Arg Leu Ser Glu Glu Lys Ile Glu Val Ile Asp Phe Ser Ser
    450                 455                 460

Tyr Ile Asp Val Ser Thr Asp Pro Gly His Tyr Ala Ile Phe Trp Glu
465                 470                 475                 480

Ile Ser Gly Glu Thr Asn Glu Asp Val Leu Gln Asp Cys Cys Asn Cys
                485                 490                 495

Leu Asp Arg Ala Phe Ile Asp Ala Gly Tyr Val Ser Ser Arg Lys Cys
            500                 505                 510

Lys Thr Ile Gly Ala Leu Glu Leu Arg Val Val Ala Lys Gly Thr Phe
        515                 520                 525

Arg Lys Ile Gln Glu His Phe Leu Gly Leu Gly Ser Ser Ala Gly Gln
    530                 535                 540

Phe Lys Met Pro Arg Cys Val Lys Pro Ser Asn Ala Lys Val Leu Gln
545                 550                 555                 560

Ile Leu Cys Glu Asn Val Val Ser Ser Tyr Phe Ser Thr Ala Phe
                565                 570                 575
```

<210> SEQ ID NO 4
<211> LENGTH: 612
<212> TYPE: PRT
<213> ORGANISM: Arabidopsis thaliana

<400> SEQUENCE: 4

```
Met Pro Glu Ala Pro Lys Lys Glu Ser Leu Glu Val Phe Asp Leu Thr
1               5                   10                  15

Leu Asp Gln Lys Asn Lys Gln Lys Leu Gln Leu Ile Glu Glu Leu Thr
            20                  25                  30

Ser Asn Ala Asp Gln Val Gln Arg Gln Val Leu Glu Glu Ile Leu Thr
        35                  40                  45

Arg Asn Ala Asp Val Glu Tyr Leu Arg Arg His Asp Leu Asn Gly Arg
    50                  55                  60

Thr Asp Arg Glu Thr Phe Lys Asn Ile Met Pro Val Ile Thr Tyr Glu
65                  70                  75                  80

Asp Ile Glu Pro Glu Ile Asn Arg Ile Ala Asn Gly Asp Lys Ser Pro
                85                  90                  95

Ile Leu Ser Ser Lys Pro Ile Ser Glu Phe Leu Thr Ser Ser Gly Thr
            100                 105                 110

Ser Gly Gly Glu Arg Lys Leu Met Pro Thr Ile Glu Glu Glu Leu Asp
        115                 120                 125

Arg Arg Ser Leu Leu Tyr Ser Leu Leu Met Pro Val Met Ser Gln Phe
    130                 135                 140

Val Pro Gly Leu Glu Asn Gly Lys Gly Met Tyr Phe Leu Phe Ile Lys
145                 150                 155                 160

Ser Glu Ser Lys Thr Pro Gly Gly Leu Pro Ala Arg Pro Val Leu Thr
                165                 170                 175

Ser Tyr Tyr Lys Ser Ser His Phe Lys Glu Arg Pro Tyr Asp Pro Tyr
            180                 185                 190

Thr Asn Tyr Thr Ser Pro Asn Glu Thr Ile Leu Cys Ser Asp Ser Tyr
        195                 200                 205

Gln Ser Met Tyr Ser Gln Met Leu Cys Gly Leu Cys Gln His Gln Glu
    210                 215                 220

Val Leu Arg Val Gly Ala Val Phe Ala Ser Gly Phe Ile Arg Ala Ile
225                 230                 235                 240

Lys Phe Leu Glu Lys His Trp Ile Glu Leu Val Arg Asp Ile Arg Thr
                245                 250                 255

Gly Thr Leu Ser Ser Leu Ile Thr Asp Pro Ser Val Arg Glu Ala Val
            260                 265                 270

Ala Lys Ile Leu Lys Pro Ser Pro Lys Leu Ala Asp Phe Val Glu Phe
        275                 280                 285

Glu Cys Lys Lys Ser Ser Trp Gln Gly Ile Ile Thr Arg Leu Trp Pro
    290                 295                 300

Asn Thr Lys Tyr Val Asp Val Ile Val Thr Gly Thr Met Ser Gln Tyr
305                 310                 315                 320

Ile Pro Thr Leu Asp Tyr Tyr Ser Asn Gly Leu Pro Leu Val Cys Thr
                325                 330                 335

Met Tyr Ala Ser Ser Glu Cys Tyr Phe Gly Val Asn Leu Arg Pro Leu
            340                 345                 350

Cys Lys Pro Ser Glu Val Ser Tyr Thr Leu Ile Pro Ser Met Ala Tyr
        355                 360                 365

Phe Glu Phe Leu Pro Val His Arg Asn Asn Gly Val Thr Asn Ser Ile
    370                 375                 380

Asn Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
```

```
                405                 410                 415

Tyr Ala Gly Leu Cys Arg Tyr Arg Val Gly Asp Leu Leu Arg Val Thr
            420                 425                 430

Gly Phe Lys Asn Lys Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
                485                 490                 495

Tyr Val Leu Phe Trp Glu Leu Cys Leu Asp Gly Asn Thr Pro Ile Pro
            500                 505                 510

Pro Ser Val Phe Glu Asp Cys Cys Leu Ala Val Glu Glu Ser Phe Asn
        515                 520                 525

Thr Val Tyr Arg Gln Gly Arg Val Ser Asp Lys Ser Ile Gly Pro Leu
    530                 535                 540

Glu Ile Lys Ile Val Glu Pro Gly Thr Phe Asp Lys Leu Met Asp Tyr
545                 550                 555                 560

Ala Ile Ser Leu Gly Ala Ser Ile Asn Gln Tyr Lys Thr Pro Arg Cys
                565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Val Pro Gly His Lys Gln
        595                 600                 605

Trp Gly Ser Asn
    610


<210> SEQ ID NO 5
<211> LENGTH: 591
<212> TYPE: PRT
<213> ORGANISM: Arabidopsis thaliana

<400> SEQUENCE: 5

Met Glu Thr Val Glu Ala Gly His Asp Asp Val Ile Gly Trp Phe Glu
1               5                   10                  15

His Val Ser Glu Asn Ala Cys Lys Val Gln Ser Glu Thr Leu Arg Arg
            20                  25                  30

Ile Leu Glu Leu Asn Ser Gly Val Glu Tyr Leu Arg Lys Trp Leu Gly
        35                  40                  45

Thr Val Asp Val Glu Lys Met Asp Asp Tyr Thr Leu Glu Thr Leu Phe
    50                  55                  60

Thr Ser Leu Val Pro Ile Val Ser His Ala Asp Leu Asp Pro Tyr Ile
65                  70                  75                  80

Gln Arg Ile Ala Asp Gly Glu Thr Ser Pro Leu Leu Thr Gln Glu Pro
                85                  90                  95

Ile Thr Val Leu Ser Leu Ser Ser Gly Thr Thr Glu Gly Arg Gln Lys
            100                 105                 110

Tyr Val Pro Phe Thr Arg His Ser Ala Gln Thr Thr Leu Gln Ile Phe
        115                 120                 125

Arg Leu Ser Ala Ala Tyr Arg Ser Arg Phe Tyr Pro Ile Arg Glu Gly
    130                 135                 140

Gly Arg Ile Leu Glu Phe Ile Tyr Ala Gly Lys Glu Phe Lys Thr Leu
145                 150                 155                 160
```

-continued

```
Gly Gly Leu Thr Val Gly Thr Ala Thr Thr His Tyr Tyr Ala Ser Glu
                165                 170                 175

Glu Phe Lys Thr Lys Gln Glu Thr Thr Lys Ser Phe Thr Cys Ser Pro
            180                 185                 190

Gln Glu Val Ile Ser Gly Gly Asp Phe Gly Gln Cys Thr Tyr Cys His
        195                 200                 205

Leu Leu Leu Gly Leu His Tyr Ser Ser Gln Val Glu Phe Val Ala Ser
    210                 215                 220

Ala Phe Ser Tyr Thr Ile Val Gln Ala Phe Ser Phe Phe Glu Glu Ile
225                 230                 235                 240

Trp Arg Glu Ile Cys Ala Asp Ile Lys Glu Gly Asn Leu Ser Ser Arg
                245                 250                 255

Ile Thr Leu Pro Lys Met Arg Lys Ala Val Leu Ala Leu Ile Arg Pro
            260                 265                 270

Asn Pro Ser Leu Ala Ser His Ile Glu Glu Ile Cys Leu Glu Leu Glu
        275                 280                 285

Thr Asn Leu Gly Trp Phe Gly Leu Ile Ser Lys Leu Trp Pro Asn Ala
    290                 295                 300

Lys Phe Ile Ser Ser Ile Met Thr Gly Ser Met Leu Pro Tyr Leu Asn
305                 310                 315                 320

Lys Leu Arg His Tyr Ala Gly Gly Leu Pro Leu Val Ser Ala Asp Tyr
                325                 330                 335

Gly Ser Thr Glu Ser Trp Ile Gly Val Asn Val Asp Pro His Leu Pro
            340                 345                 350

Pro Glu Asp Val Ser Phe Ala Val Ile Pro Thr Phe Ser Tyr Phe Glu
        355                 360                 365

Phe Ile Pro Leu Tyr Arg Arg Gln Asn Gln Ser Asp Ile Cys Ile Asp
    370                 375                 380

Gly Asp Phe Val Glu Asp Lys Pro Val Pro Leu Ser Gln Val Lys Leu
385                 390                 395                 400

Gly Gln Glu Tyr Glu Leu Val Leu Thr Thr Phe Thr Gly Leu Tyr Arg
                405                 410                 415

Tyr Arg Leu Gly Asp Val Val Glu Val Thr Ser Phe His Lys Gly Thr
            420                 425                 430

Pro Lys Leu Ser Phe Ile Tyr Arg Arg Lys Leu Ile Leu Thr Ile Asn
        435                 440                 445

Ile Asp Lys Asn Thr Glu Lys Asp Leu Gln Arg Val Val Asp Lys Ala
    450                 455                 460

Ser Gln Leu Leu Ser Arg Ser Thr Arg Ala Glu Val Val Asp Phe Thr
465                 470                 475                 480

Ser His Ala Asp Val Ile Ala Arg Pro Gly His Tyr Val Ile Tyr Trp
                485                 490                 495

Glu Ile Arg Gly Glu Ala Asp Asp Lys Ala Leu Glu Glu Cys Cys Arg
            500                 505                 510

Glu Met Asp Thr Ala Phe Val Asp Tyr Gly Tyr Val Val Ser Arg Arg
        515                 520                 525

Met Asn Ser Ile Gly Pro Leu Glu Leu Arg Val Val Glu Arg Gly Thr
    530                 535                 540

Phe Gly Lys Val Ala Glu Arg Cys Val Gly Lys Cys Gly Gly Leu Asn
545                 550                 555                 560

Gln Phe Lys Thr Pro Arg Cys Thr Thr Asn Ser Val Met Leu Asp Ile
                565                 570                 575

Leu Asn Asp Ser Thr Ile Lys Arg Phe Arg Ser Ser Ala Tyr Asp
```

580 585 590

<210> SEQ ID NO 6
<211> LENGTH: 575
<212> TYPE: PRT
<213> ORGANISM: Arabidopsis thaliana

<400> SEQUENCE: 6

```
Met Lys Pro Ile Phe Asp Ile Asn Glu Thr Phe Glu Lys Gln Leu Lys
1               5                   10                  15

Asp Leu Thr Ser Asn Val Lys Ser Ile Gln Asp Asn Leu Leu Glu Glu
            20                  25                  30

Ile Ile Thr Pro Asn Thr Lys Thr Glu Tyr Leu Gln Arg Phe Leu Ile
        35                  40                  45

Asp Arg Phe Asp Lys Glu Leu Phe Lys Lys Asn Val Pro Ile Val Ser
    50                  55                  60

Tyr Glu Asp Ile Lys Pro Tyr Leu Asp Arg Val Val Asn Gly Glu Ser
65                  70                  75                  80

Ser Asp Val Ile Ser Ala Arg Thr Ile Thr Gly Phe Leu Leu Ser Ser
                85                  90                  95

Gly Thr Ser Gly Gly Ala Gln Lys Met Met Pro Trp Asn Asn Lys Tyr
            100                 105                 110

Leu Asp Asn Leu Thr Phe Ile Tyr Asp Leu Arg Met Gln Val Ile Thr
        115                 120                 125

Lys His Val Lys Gly Val Glu Glu Gly Lys Gly Met Met Phe Leu Phe
    130                 135                 140

Thr Lys Gln Glu Ser Met Thr Pro Ser Gly Leu Pro Ala Arg Val Ala
145                 150                 155                 160

Thr Ser Ser Tyr Phe Lys Ser Asp Tyr Phe Lys Asn Arg Pro Ser Asn
                165                 170                 175

Trp Tyr Tyr Ser Tyr Thr Ser Pro Asp Glu Val Ile Leu Cys Pro Asn
            180                 185                 190

Asn Thr Glu Ser Leu Tyr Cys His Leu Leu Cys Gly Leu Val Gln Arg
        195                 200                 205

Asp Glu Val Val Arg Thr Gly Ser Ile Phe Ala Ser Val Met Val Arg
    210                 215                 220

Ala Ile Glu Val Leu Lys Asn Ser Trp Glu Glu Leu Cys Ser Asn Ile
225                 230                 235                 240

Arg Ser Gly His Leu Ser Asn Trp Val Thr Asp Leu Gly Cys Gln Asn
                245                 250                 255

Ser Val Ser Leu Val Leu Gly Gly Pro Arg Pro Glu Leu Ala Asp Thr
            260                 265                 270

Ile Glu Glu Ile Cys Asn Gln Asn Ser Trp Lys Gly Ile Val Lys Arg
        275                 280                 285

Leu Trp Pro Asn Thr Lys Tyr Ile Glu Thr Val Val Thr Gly Ser Met
    290                 295                 300

Gly Gln Tyr Val Pro Met Leu Asn Tyr Tyr Cys Asn Asp Leu Pro Leu
305                 310                 315                 320

Val Ser Thr Thr Tyr Gly Ser Ser Glu Thr Thr Phe Gly Ile Asn Leu
                325                 330                 335

Asp Pro Leu Cys Lys Pro Glu Asp Val Ser Tyr Thr Phe Met Pro Asn
            340                 345                 350

Met Ser Tyr Phe Glu Phe Ile Pro Met Asp Gly Gly Asp Lys Asn Asp
        355                 360                 365
```

```
Val Val Asp Leu Glu Asp Val Lys Leu Gly Cys Thr Tyr Glu Pro Val
    370                 375                 380

Val Thr Asn Phe Ala Gly Leu Tyr Arg Met Arg Val Gly Asp Ile Val
385                 390                 395                 400

Leu Val Thr Gly Phe Tyr Asn Asn Ala Pro Gln Phe Lys Phe Val Arg
                405                 410                 415

Arg Glu Asn Val Val Leu Ser Ile Asp Ser Asp Lys Thr Asn Glu Glu
            420                 425                 430

Asp Leu Phe Lys Ala Val Ser Gln Ala Lys Leu Val Leu Glu Ser Ser
        435                 440                 445

Gly Leu Asp Leu Lys Asp Phe Thr Ser Tyr Ala Asp Thr Ser Thr Phe
    450                 455                 460

Pro Gly His Tyr Val Val Tyr Leu Glu Val Asp Thr Lys Glu Gly Glu
465                 470                 475                 480

Glu Lys Glu Thr Ala Gln Phe Glu Leu Asp Glu Glu Ala Leu Ser Thr
                485                 490                 495

Cys Cys Leu Val Met Glu Glu Ser Leu Asp Asn Val Tyr Lys Arg Cys
            500                 505                 510

Arg Phe Lys Asp Gly Ser Ile Gly Pro Leu Glu Ile Arg Val Val Arg
        515                 520                 525

Gln Gly Thr Phe Asp Ser Leu Met Asp Phe Phe Ile Ser Gln Gly Ala
    530                 535                 540

Ser Thr Gly Gln Tyr Lys Thr Pro Arg Cys Ile Lys Ser Gly Lys Ala
545                 550                 555                 560

Leu Gln Val Leu Glu Thr Cys Val Val Ala Lys Phe Phe Ser Ile
                565                 570                 575


<210> SEQ ID NO 7
<211> LENGTH: 609
<212> TYPE: PRT
<213> ORGANISM: Arabidopsis thaliana

<400> SEQUENCE: 7

Met Ile Pro Ser Tyr Asp Pro Asn Asp Thr Glu Ala Gly Leu Lys Leu
1               5                   10                  15

Leu Glu Asp Leu Thr Thr Asn Ala Glu Ala Ile Gln Gln Gln Val Leu
            20                  25                  30

His Gln Ile Leu Ser Gln Asn Ser Gly Thr Gln Tyr Leu Arg Ala Phe
        35                  40                  45

Leu Asp Gly Glu Ala Asp Lys Asn Gln Gln Ser Phe Lys Asn Lys Val
    50                  55                  60

Pro Val Val Asn Tyr Asp Asp Val Lys Pro Phe Ile Gln Arg Ile Ala
65                  70                  75                  80

Asp Gly Glu Ser Ser Asp Ile Val Ser Ala Gln Pro Ile Thr Glu Leu
                85                  90                  95

Leu Thr Ser Ser Gly Thr Ser Ala Gly Lys Pro Lys Leu Met Pro Ser
            100                 105                 110

Thr Ala Glu Glu Leu Glu Arg Lys Thr Phe Phe Tyr Ser Met Leu Val
        115                 120                 125

Pro Ile Met Asn Lys Tyr Val Asp Gly Leu Asp Glu Gly Lys Gly Met
    130                 135                 140

Tyr Leu Leu Phe Ile Lys Pro Glu Ile Lys Thr Pro Ser Gly Leu Met
145                 150                 155                 160

Ala Arg Pro Val Leu Thr Ser Tyr Tyr Lys Ser Gln His Phe Arg Asn
                165                 170                 175
```

```
Arg Pro Phe Asn Lys Tyr Asn Val Tyr Thr Ser Pro Asp Gln Thr Ile
            180                 185                 190

Leu Cys Gln Asp Ser Lys Gln Ser Met Tyr Cys Gln Leu Leu Cys Gly
        195                 200                 205

Leu Val Gln Arg Ser His Val Leu Arg Val Gly Ala Val Phe Ala Ser
    210                 215                 220

Ala Phe Leu Arg Ala Val Lys Phe Leu Glu Asp His Tyr Lys Glu Leu
225                 230                 235                 240

Cys Ala Asp Ile Arg Thr Gly Thr Val Thr Ser Trp Ile Thr Asp Ser
                245                 250                 255

Ser Cys Arg Asp Ser Val Leu Ser Ile Leu Asn Gly Pro Asn Gln Glu
            260                 265                 270

Leu Ala Asp Glu Ile Glu Ser Glu Cys Ala Glu Lys Ser Trp Glu Gly
        275                 280                 285

Ile Leu Arg Arg Ile Trp Pro Lys Ala Lys Tyr Val Glu Val Ile Val
    290                 295                 300

Thr Gly Ser Met Ala Gln Tyr Ile Pro Thr Leu Glu Phe Tyr Ser Gly
305                 310                 315                 320

Gly Leu Pro Leu Val Ser Thr Met Tyr Ala Ser Ser Glu Cys Tyr Phe
                325                 330                 335

Gly Ile Asn Leu Asn Pro Leu Cys Asp Pro Ala Asp Val Ser Tyr Thr
            340                 345                 350

Leu Leu Pro Asn Met Ala Tyr Phe Glu Phe Leu Pro Val Asp Asp Lys
        355                 360                 365

Ser His Glu Glu Ile His Phe Ala Thr His Ser Asn Thr Asp Asp Asp
    370                 375                 380

Asp Asp Ala Leu Lys Glu Asp Leu Ile Val Asn Leu Val Asn Val Glu
385                 390                 395                 400

Val Gly Gln Tyr Tyr Glu Ile Val Ile Thr Thr Phe Thr Gly Leu Tyr
                405                 410                 415

Arg Tyr Arg Val Gly Asp Ile Leu Lys Val Thr Gly Phe His Asn Lys
            420                 425                 430

Ala Pro Gln Phe Arg Phe Val Gln Arg Arg Asn Val Val Leu Ser Ile
        435                 440                 445

Asp Thr Asp Lys Thr Ser Glu Glu Asp Leu Leu Asn Ala Val Thr Gln
    450                 455                 460

Ala Lys Leu Asn His Leu Gln His Pro Ser Ser Leu Leu Leu Thr Glu
465                 470                 475                 480

Tyr Thr Ser Tyr Ala Asp Thr Ser Ser Ile Pro Gly His Tyr Val Leu
                485                 490                 495

Phe Trp Glu Leu Lys Pro Arg His Ser Asn Asp Pro Pro Lys Leu Asp
            500                 505                 510

Asp Lys Thr Met Glu Asp Cys Cys Ser Glu Val Glu Asp Cys Leu Asp
        515                 520                 525

Tyr Val Tyr Arg Arg Cys Arg Asn Arg Asp Lys Ser Ile Gly Pro Leu
    530                 535                 540

Glu Ile Arg Val Val Ser Leu Gly Thr Phe Asp Ser Leu Met Asp Phe
545                 550                 555                 560

Cys Val Ser Gln Gly Ser Ser Leu Asn Gln Tyr Lys Thr Pro Arg Cys
                565                 570                 575

Val Lys Ser Gly Gly Ala Leu Glu Ile Leu Asp Ser Arg Val Ile Gly
            580                 585                 590
```

```
Arg Phe Phe Ser Lys Arg Val Pro Gln Trp Glu Pro Leu Gly Leu Asp
        595                 600                 605

Ser


<210> SEQ ID NO 8
<211> LENGTH: 597
<212> TYPE: PRT
<213> ORGANISM: Synechococcus PCC 7335

<400> SEQUENCE: 8

Met Val Ile His Thr Ile Pro Lys Glu Ile Leu Asp Ser Val Ala Ser
1               5                   10                  15

Thr Gly Asp Val Phe Ala Tyr His Leu Leu Arg Ser Thr Gly Asp Ile
            20                  25                  30

Gly Glu Thr Val Leu Gln Tyr Leu Leu Cys Leu Ala Ala Lys Val Asn
        35                  40                  45

Leu Thr Gly Ile Glu Gln Asp Thr Tyr Asn Ala Asp Lys Val Gln Glu
    50                  55                  60

Gln Leu Leu Asn Asp Ile Leu Arg Ser Glu Asn Lys Thr Leu Tyr Gly
65                  70                  75                  80

Lys Lys Tyr Asn Phe Asp Ser Leu Asn Val Asp Ser Phe Arg Ser Ser
                85                  90                  95

Leu Pro Leu Thr Ser Tyr Glu Asn Tyr Arg Glu Ser Ile Asp Asn Val
            100                 105                 110

Val Gln Thr Gly Asn Tyr Ser Gln Leu Val Ser Glu Pro Ile Thr Leu
        115                 120                 125

Phe Gln Glu Ser Ser Gly Thr Thr Gly Lys Val Lys Leu Ile Pro Arg
    130                 135                 140

Thr Asn Lys Phe Thr Leu Ser Ala Met Arg Ala Phe Gln Ala Ile Glu
145                 150                 155                 160

Ala Val Val Gln Ser His Phe Gln Asn Pro Ser Ser Ser Ser Gln Arg
                165                 170                 175

Val Leu Ala Leu Val Asn Thr Ser Pro Thr Lys Leu Thr Pro Thr Gly
            180                 185                 190

Ile Pro Arg Gly Thr Gly Thr Ser Gly Gly Leu Asn Asp Ala Leu Gln
        195                 200                 205

Lys Phe Lys Leu Ala Asn Tyr Leu Ile Asp Ile Lys Tyr Ser Ser Pro
    210                 215                 220

Ser Pro Val Phe Leu Ile Ser Asn Thr Glu Ala Ala Tyr Tyr Cys His
225                 230                 235                 240

Leu Leu Phe Gly Leu Leu Asp Ser Asp Ile Asn Asp Ile Ser Ala Asn
                245                 250                 255

Phe Ala Ala Thr Val Leu Asn Ala Met Lys Ile Leu Glu Lys Ala Trp
            260                 265                 270

Thr Gln Leu Val Glu Asp Ile Arg Gln Gly Lys Leu Tyr Ala Gly Leu
        275                 280                 285

Asp Ile Asp Glu Ala Thr Arg Arg Glu Leu Glu Ile Arg Leu Arg Ala
    290                 295                 300

Asn Pro Glu Arg Ala Arg Glu Leu Gln Ala Tyr Phe Glu Glu Gly Phe
305                 310                 315                 320

Glu Gly Ile Leu Pro Arg Ile Trp Pro Ser Leu Ser Cys Ile Gln Cys
                325                 330                 335

Ile Thr Thr Gly Ser Met Gln Leu Tyr Thr Asp Ala Leu Arg Tyr Tyr
            340                 345                 350
```

```
Ser Gly Thr Val Pro Phe Phe Ser Gly Ser Tyr Gly Ala Ser Glu Ala
        355                 360                 365

Trp Ile Gly Val Asn Leu Asp Pro Glu Arg Glu Pro Pro Ala Phe Val
    370                 375                 380

Val Thr Pro His Thr Ala Phe Phe Glu Phe Ile Pro Gln Asp Ala Ile
385                 390                 395                 400

Asp Gln Glu Gln Ser Ala Thr Val Cys Leu Thr Asp Leu Lys Pro Gly
                405                 410                 415

Glu Ser Tyr Glu Val Val Val Thr Asn Met Ser Gly Leu Tyr Arg Tyr
            420                 425                 430

Arg Val Gly Asp Val Val Arg Cys Val Gly Tyr His His Lys Ser Pro
        435                 440                 445

Met Ile Glu Phe Met Tyr Arg Arg Gln Thr Leu Leu Asn Leu Phe Gly
    450                 455                 460

Glu Lys Val Ser Glu Asp Val Ile Tyr Ser Ala Leu Ser Thr Thr Leu
465                 470                 475                 480

Arg Glu Phe Gly Met Ala Ile Gln Asp Ile Asp Tyr Thr Cys Arg His
                485                 490                 495

Glu Phe Glu Gly Thr Pro Trp Arg Tyr Val Val Tyr Leu Glu Pro Ala
            500                 505                 510

Asp Tyr Glu Gly Cys Ser Ser Gln His Glu Met Val Gln Gln Arg Leu
        515                 520                 525

Asp Glu Val Leu Cys Asn Leu Ser Asp Arg Tyr Arg Gln Leu Arg Glu
    530                 535                 540

Val Gly Ser Ile Gly Ser Leu Lys Leu Lys Leu Val Arg Glu Gly Thr
545                 550                 555                 560

Phe Ser Gly Leu Lys Thr Arg Leu Leu Ser Gln Glu His Ser Asp Ser
                565                 570                 575

Gln Phe Lys Met Pro Arg Leu Leu Thr Glu Thr Ala Leu Ile Ser Phe
            580                 585                 590

Met Glu Ser Ser Leu
        595


<210> SEQ ID NO 9
<211> LENGTH: 548
<212> TYPE: PRT
<213> ORGANISM: Cystobacter fuscus

<400> SEQUENCE: 9

Met Gln Ala Ala Gly Arg Arg Asp Lys Gln Arg Phe Ile Glu Gln Thr
1               5                   10                  15

Arg His Val Ala Arg Val Asn Val Asp Thr Leu Arg Ala Ile Leu Gln
            20                  25                  30

His Asn Arg Asp Thr Asp Phe Gly Arg Arg His Gly Phe Ala Ser Leu
        35                  40                  45

Arg Thr Val Glu Asp Phe Gln Arg Ala Leu Pro Val Ser Thr Tyr Glu
    50                  55                  60

Pro Phe Arg Pro Tyr Met Glu Arg Ile Ala Arg Gly Glu Gln Asn Val
65                  70                  75                  80

Leu Thr Ala Asp Arg Val Glu Tyr Leu Gly Ile Thr Ser Gly Thr Thr
                85                  90                  95

Gly Gln Arg Lys Leu Leu Pro Val Ser Arg Pro His Leu Glu Asn Met
            100                 105                 110

Arg Arg Thr Met Met Ile Gly Arg Ala Val Val Thr Glu Lys Val Pro
        115                 120                 125
```

```
Ala Ala Arg Arg Pro Ser Arg Gly Met Ile Leu Met Asn Ala Val Leu
    130                 135                 140

Arg Glu Arg Ser Glu Gly Gly Leu Leu Thr Gly Ala Leu Thr Ala Ile
145                 150                 155                 160

Ser Thr His Ser Met Gly Arg Ala Ala Ser Phe Ala Phe Thr Ser Pro
                165                 170                 175

Pro Glu Ala Phe Arg Leu Arg Lys His Ala Asp Ala Leu Tyr Leu His
            180                 185                 190

Leu Leu Phe Gly Leu Arg Glu Arg Glu Leu Gly Thr Leu Met Ala Pro
        195                 200                 205

Phe Ala Ser Gly Leu Leu Asp Met Val His Leu Leu Glu Arg Arg Gly
    210                 215                 220

Ala Asp Leu Val Asp Asp Ile Ala Arg Gly Val Leu Arg Pro Glu Leu
225                 230                 235                 240

Asp Leu Glu Pro Glu Gln Arg Arg Leu Leu Gln Ser Arg Leu Leu Pro
                245                 250                 255

Asp Pro Glu Arg Ala Arg Glu Val Ser Gln Ala Leu Glu Gln Gly Pro
            260                 265                 270

His Gly Leu Leu Arg Arg Leu Trp Pro Arg Leu Ala Tyr Val Ser Ser
        275                 280                 285

Ile Thr Gly Ala Ser Phe Ser Leu Tyr Thr Arg Gln Leu Thr Pro Tyr
    290                 295                 300

Leu Glu Gly Val Pro Leu Ser Ala Ala Ser Tyr Val Ser Thr Glu Gly
305                 310                 315                 320

Ile Leu Gly Val Pro Leu Glu Leu Glu Gln Ala Val Tyr Cys Leu Met
                325                 330                 335

Val Gly Met Ala Phe Phe Glu Phe Ile Pro Glu Arg Glu Leu Asp Ala
            340                 345                 350

Glu Ser Pro Thr Thr Leu Leu Pro Glu Gln Leu Val Glu Gly Glu Ala
        355                 360                 365

Tyr Glu Val Val Leu Thr Thr Gln Ala Gly Leu Tyr Arg Tyr Arg Leu
    370                 375                 380

Gly Asp Val Val Arg Ile Val Gly Arg Tyr His Glu Ala Pro Leu Met
385                 390                 395                 400

Glu Phe Leu Tyr Arg Arg Gly Ala Leu Leu Asn Leu Met Gly Glu Lys
                405                 410                 415

Thr Ser Glu His Ala Ala Arg Leu Ala Leu Glu Gln Ala Leu Ala Thr
            420                 425                 430

Glu Gly Leu Leu Pro Ala Asp Tyr Ser Val Val Glu Glu Thr Glu Thr
        435                 440                 445

Leu Pro Gly Arg Tyr Ala Leu Phe Val Glu Leu Gln Glu Gly Ala Arg
    450                 455                 460

Pro Gln Gly Ala Pro Glu Gln Leu Ser Arg Ala Leu Glu Glu Ala Leu
465                 470                 475                 480

Cys Arg Thr Asn Pro Phe Tyr Glu Val Ile Arg Arg Ser Glu Arg Leu
                485                 490                 495

Gly Ala Ala Gln Leu His Arg Val Glu Pro Gly Thr Phe Gln Ala Leu
            500                 505                 510

Arg Asp Val Leu Val Gln Arg Gly Ala Ser Pro Thr Gln Val Lys Val
        515                 520                 525

Pro Arg Val Val Arg Asp Ala Glu Leu Gln Gly Leu Leu Arg Gln Arg
    530                 535                 540
```

Arg Val Thr Gly
545

<210> SEQ ID NO 10
<211> LENGTH: 395
<212> TYPE: PRT
<213> ORGANISM: Pseudomonas savastanoi

<400> SEQUENCE: 10

Met Thr Ala Tyr Asp Met Glu Lys Glu Trp Ser Arg Ile Ser Ile Thr
1 5 10 15

Ala Ala Lys Ile His Gln Asn Asn Asp Phe Glu Gly Phe Thr Tyr Gln
20 25 30

Asp Phe Arg Thr His Val Pro Ile Met Asp Lys Asp Gly Phe Ala Ala
35 40 45

Gln Thr Glu Arg Cys Leu Glu Arg Asn Glu Arg Asn Cys Leu Ile Gly
50 55 60

Phe Thr Ser Gly Thr Ser Gly Asn Ile Lys Arg Cys Tyr Tyr Tyr Tyr
65 70 75 80

Asp Cys Glu Val Asp Glu Asp Ser Ser Leu Ser Asn Val Phe Arg Ser
85 90 95

Asn Gly Phe Ile Leu Pro Gly Asp Arg Cys Ala Asn Leu Phe Thr Ile
100 105 110

Asn Leu Phe Ser Ala Leu Asn Asn Thr Ile Thr Met Met Ala Gly Asn
115 120 125

Cys Gly Ala His Val Val Ser Val Gly Asp Ile Thr Leu Val Thr Lys
130 135 140

Ser His Phe Glu Ala Leu Asn Ser Ile Lys Leu Asn Val Leu Leu Gly
145 150 155 160

Val Pro Ser Thr Ile Leu Gln Phe Ile Asn Ala Met Gln His Asn Gly
165 170 175

Val His Ile Asn Ile Glu Lys Val Val Phe Thr Gly Glu Ser Leu Lys
180 185 190

Thr Phe Gln Lys Lys Ile Ile Arg Gln Ala Phe Gly Glu Gln Val Ser
195 200 205

Ile Val Gly Val Tyr Gly Ser Ser Glu Gly Gly Ile Leu Gly Phe Thr
210 215 220

Asn Ser Pro Cys His Thr Glu Tyr Glu Phe Leu Ser Asp Lys Tyr Phe
225 230 235 240

Ile Glu Lys Glu Gly Asp Ser Ile Leu Ile Thr Ser Leu Thr Arg Glu
245 250 255

Asn Phe Thr Pro Leu Leu Arg Tyr Arg Leu Gly Asp Thr Ala Thr Leu
260 265 270

Ser Met Lys Gly Asp Lys Leu Tyr Leu Thr Asp Ile Gln Arg Glu Asp
275 280 285

Met Ser Phe Asn Phe Met Gly Asn Leu Ile Gly Leu Gly Ile Ile Gln
290 295 300

Gln Thr Ile Lys Gln Thr Leu Gly Arg Ser Leu Glu Ile Gln Val His
305 310 315 320

Leu Ser Val Thr Glu Glu Arg Lys Glu Leu Val Thr Val Phe Val Gln
325 330 335

Ala Ser Glu Val Asp Glu Asp Glu Arg Val Arg Ile Glu Thr Ala Ile
340 345 350

Ala Asp Ile Pro Asp Ile Lys Glu Ala Tyr Gln Lys Asn Gln Gly Thr
355 360 365

```
Val Ser Val Leu Arg Lys Asp Ala Arg Asp Tyr Ala Val Ser Glu Arg
    370                 375                 380

Gly Lys Met Leu Tyr Ile Ile Asp Arg Arg Asn
385                 390                 395


<210> SEQ ID NO 11
<211> LENGTH: 398
<212> TYPE: PRT
<213> ORGANISM: Pantoea agglomerans

<400> SEQUENCE: 11

Met Arg Ser Tyr Asp His Gln Pro Thr Phe Val Glu Gln His Asn Arg
1               5                   10                  15

Ile Ser Ile Ile Ser Gly Ser Thr Phe Arg Asp Tyr Glu His Phe Ala
            20                  25                  30

Arg Ser Val Pro Ile Ser Lys Leu Val Arg Met His Glu Val Glu Gly
        35                  40                  45

Lys Gln Gly Asp Asp Ser Ser Ala Asn Leu Pro Ser Leu Ile Gly Ala
    50                  55                  60

Thr Ser Gly Thr Ser Gly Lys Met Lys Pro Val Arg Ile Gln Leu Lys
65                  70                  75                  80

Asn Gly Gly Cys Ser Val Ser Ala Ser Glu Arg Asn Phe Ile Tyr His
                85                  90                  95

Leu Arg Glu Arg Arg Val Phe Phe Pro Gln Asp Val Val Gly Asn Leu
            100                 105                 110

Phe Thr Ile Asn Leu Phe Ser Thr Leu His Gln Ser Ala Cys Asp Ile
        115                 120                 125

Val Lys Tyr Cys Gln Gly Ser Ile Val Pro Val Gly Asp Ile Ala Leu
    130                 135                 140

Leu Thr Arg Asp His Phe Leu Phe Leu Gln Glu Val Glu Leu Ser Val
145                 150                 155                 160

Leu Phe Gly Val Pro Ala Thr Ile Ile Gln Phe Val Glu Ala Met Leu
                165                 170                 175

Ser Asn Lys Val Pro Ile Gly Ile Lys Lys Ile Val Phe Thr Gly Glu
            180                 185                 190

Thr Leu Arg Pro Ser Gln Ala Glu Trp Leu Arg Ser Arg Leu Gly Arg
        195                 200                 205

Thr Leu Ser Ile Val Gly Leu Tyr Gly Leu Ser Glu Cys Gly Phe Leu
    210                 215                 220

Gly Leu Thr Asp Ala Gln Asp Cys Asp Glu Tyr Thr Leu Phe Asn Asp
225                 230                 235                 240

Asp Phe Phe Phe Glu Gln Asp Pro Val His Gly Leu Leu Val Thr Ser
                245                 250                 255

Leu Asp Pro Ser Ala Lys Asn Arg Leu Ile Arg Tyr Pro Thr Gly Asp
            260                 265                 270

Gly Val Glu Leu Thr Phe His Asn Lys Gln Leu Lys Met Arg Ile Met
        275                 280                 285

Ala Arg Lys Asp Leu Leu Phe Asn Phe Val Gly Asn Leu Ile Ser Val
    290                 295                 300

Glu Ser Ile Ala Ala Thr Val Ala Glu Ser Ile Pro Glu Ser Phe Ile
305                 310                 315                 320

Gln Leu Val Ile Arg Ser Glu Lys Gly Gln Gln Glu Leu Leu Leu Val
                325                 330                 335

Asn Val Ala Gly Lys Asn Leu Gln Thr Gln Gln Leu Glu Leu Ile Ala
```

```
            340                 345                 350

Gln Lys Leu Arg Ala Arg Pro Glu Leu Ala Glu Val Tyr Gln Lys Gln
        355                 360                 365

Arg Gly Arg Leu Glu Val His Ser Val Ala Glu Asn Ala Phe Val Leu
    370                 375                 380

Ser Ala Arg Gly Lys His Gln Phe Val Val Asp Glu Arg Glu
385                 390                 395


<210> SEQ ID NO 12
<211> LENGTH: 1839
<212> TYPE: DNA
<213> ORGANISM: Arabidopsis thaliana

<400> SEQUENCE: 12

atgccggaag caccaaaaat cgcagcctta gaagtcagtg atgagagcct ggctgagaaa      60

aacaaaaaca agctgcaatt tatcgaagat gttaccacca acgctgacga tgtgcaacgt     120

cgcgttctgg aagaaattct gagtcgtaat gcggacgtag aatatctgaa acgccatggt     180

ctggaaggcc gaaccgatcg cgagaccttc aagcacatca tgccggttgt gacgtacgaa     240

gatatccaac ccgaaatcaa ccgtattgcg aatggcgaca aatcgcaggt tctgtgttcg     300

aacccgataa gcgagtttct caccagttcc ggtacctcag gcggagaacg caaacttatg     360

ccgacgatcg aggaagaact ggatcgtcgg agtctgctgt actcactcct tatgcccgtc     420

atggatcagt ttgttccggg gttagataaa gggaaaggga tgtacttcct cttcatcaag     480

tcggaatcga aaacccctgg tggtctgcct gcacgtcccg tcctgacctc gtattacaag     540

tcctctcact tcaagaatcg accttacgat ccgtatacca actataccag tccgaatcag     600

acgatcttgt gttccgactc ctaccaatcg atgtacagcc agatgctttg cggtctgtgt     660

cagcacaaag aagtgctgcg tgttggcgcg gtttttgcca gcgggtttat tcgcgcaatc     720

aaatttctgg agaaacactg gccggaattg gcgcgcgaca ttcgcacagg cactctgagc     780

agcgaaatta cggattccag cgttcgcgaa gcagtgggcg agattctgaa acccgatcct     840

aaactggcgg atttcgtcga aagtgaatgt cgcaaaacat cttggcaggg aattattacg     900

cggctatggc caaataccaa atatgttgac gtgattgtca ctggcaccat gagccagtac     960

attccgacac ttgactatta ctcgaacggc ttaccgttag tctgcacgat gtatgcgagc    1020

agtgaatgct actttggagt gaatctcagg ccactatgca aaccatctga agtatcttac    1080

acccttatcc cgaacatggc ctatttcgag ttccttccgg tccatcgtaa ctcaggcgta    1140

actagcagca ttagcttgcc taaagcactg accgaaaaag aacaacagga gttagtagat    1200

ctggtagacg tgaagctggg ccaggaatat gagttagtcg tcacaacgta tgccggtctg    1260

tatcggtatc gcgtgggtga tgtgctgagt gtagccggat tcaaaaataa tgctccgcag    1320

tttagcttta tctgccgtaa aaacgtggtt ctctccattg actctgacaa gacggatgaa    1380

gtggaattgc aaaatgctgt gaaaaacgcc gtaacgcatc tggttccgtt tgatgcctca    1440

ctgtcagaat atacctcgta tgcggatact tcttctattc caggtcatta cgtgctgttc    1500

tgggaattgt gtctgaatgg caacactccg atacctccgt ctgtgtttga ggattgctgc    1560

ttgaccattg aagagagctt aaatagcgtg tatcgccaag gccgtgtgtc cgacaaaagc    1620

attggtccac tggagatcaa gatggtggaa tcgggtactt ttgataagtt gatggattat    1680

gcgatttctt taggcgcgtc catcaaccag tacaaaacac caagatgcgt caaattcgcg    1740

ccgattatcg agctcctgaa ctcacgtgtg gttgacagct atttttcccc caaatgtccg    1800
```

aaatggtcac cggggcataa acagtggggt agtaattaa 1839

<210> SEQ ID NO 13
<211> LENGTH: 1818
<212> TYPE: DNA
<213> ORGANISM: Oryza sativa

<400> SEQUENCE: 13
atggctgtga tgacggatgt gtccacgacg ggcacggcac tgcgtacccc ggcggctggc 60
gctgttaaag aaggcgatgt tgaaaaactg cgttttattg atgaaatgac cacgaacgtg 120
gacgcagttc aggaacgtgt gctgggcgaa atcctgggtc gcaatgcggg caccgaatat 180
ctgacgaaat gcggtctgga tggtgcaacc gaccgtgcag cctttcgcgc taaagtgccg 240
gttgttagtt acgatgacct gcagccgtat attcaacgta tcgccaacgg cgatcgcagt 300
ccgattctgt ccacgcatcc ggttagcgaa tttctgacca gctctggtac gtctgcaggc 360
gaacgcaaac tgatgccgac catcatggat gaactggacc gtcgccagct gctgtacagc 420
ctgctgatgc cggtgatgaa tctgtatgtt ccgggtctgg ataaaggcaa aggtctgtac 480
tttctgttcg tgaaatctga aaccaaaacg ccgggcggtc tgaccgcacg tccggttctg 540
acgtcatact acaaatcgga tcatttcaaa aaccgcccgt atgacccgta ccacaattat 600
acctcaccga cggcagctat tctgtgtgca gatgctttcc agtcgatgta tgcccaaatg 660
gtgtgcggcc tgtgtcagcg taacgacgtt ctgcgcctgg gtgcagtctt tgcttctggc 720
ctgctgcgtg cgattcgctt cctgcagctg aattgggaac aactggccga tgacatcgaa 780
agtggtgaac tgaccccgcg tgtgacggat ccgtccgtcc gtgaagcagt ggcagcaatt 840
ctgctgccgg acccggaact ggcgaaactg atccgtgccg aatgcagtaa gggtgattgg 900
gccggcatta tcacccgcgt ttggccgaac acgaaatatc tggacgtcat tgtgacgggt 960
gcaatggcac agtacatccc gaccctggaa ttttattccg gcggtctgcc gatggcatgc 1020
accatgtacg ctagttccga atgttatttc ggcctgaacc tgcgtccgat gtgtgatccg 1080
tcagaagtgt cgtacaccat catgccgaat atgggttatt ttgaatttct gccggttgat 1140
gaaacgggtg cagctagcgg tgatgcaacc cagctggtcg acctggcccg tgttgaagtc 1200
ggtcgcgaat atgaactggt tattaccacg tacgcgggtc tgaatcgtta tcgcgtcggc 1260
gatgtgctgc gtgttaccgg ttttcacaac gcggccccgc aatttcgctt cgtccgtcgc 1320
aaaaatgtgc tgctgagcat cgaatctgat aaaaccgacg aagcggaact gcagcgtgcc 1380
gtggaacgcg catcagctct gctgcgtccg catggcgcga gtgtcgtgga atacacctcc 1440
caagcctgca cgaaacgcat tccgggtcac tacgttatct attgggaact gctgaccaaa 1500
ggtgcaggtg caacggttgt cgatgcagac accctgggcc gttgctgtct ggaaatggaa 1560
gaagcactga acacggtgta tcgtcagtca cgcgttgctg atggctcgat tggtccgctg 1620
gaaatccgtg tggttcgccc gggcaccttt gaagaactga tggattacgc aattagccgt 1680
ggtgcttcta tcaatcaata taaagttccg cgctgtgtca ccttcccgcc gattgtcgaa 1740
ctgctggata gccgcgtggt ttcatcacac ttttcaccgg ccctgccgca ttggaccccg 1800
gctcgtcgtt cggaataa 1818

<210> SEQ ID NO 14
<211> LENGTH: 1728
<212> TYPE: DNA
<213> ORGANISM: Arabidopsis thaliana

<400> SEQUENCE: 14

```
atgctggaga aagtcgaaac ctttgacatg aaccgcgtga ttgatgaatt tgatgaaatg     60
acccgtaacg cacaccaagt tcagaaacag acgctgaaag agattcttct caagaaccag    120
agtgctatct atctgcagaa ttgtgggtta aatggtaatg cgacagatcc ggaagaagcg    180
tttaaatcca tggttccgct ggtaacggat gtggaactgg aaccatacat caaacggatg    240
gttgacggag acacgtcgcc gattttaacc ggtcatcctg tgccggcaat cagcctgtca    300
tcgggtactt cgcaaggccg ccccaagttc attccgttta ccgatgagct gatggaaaac    360
actctgcagt tattccgcac ggcatttgcg ttccgcaatc gcgacttccc aattgacgat    420
aatgggaaag ccctccagtt cattttctct agcaagcagt acatttccac gggaggtgtt    480
cctgtcggca cagcgactac gaacgtatat cgtaatccga attttaaagc gggcatgaag    540
tcaatcacct ctccgagttg cagtcctgat gaagtgattt tcagcccaga tgtccatcaa    600
gctctgtatt gccacttatt gagcggcatt cttttccgtg atcaggtcca atacgtgttt    660
gctgtgtttg cgcatggtct tgtgcatgcc tttcgcacct ttgaacaggt atgggaagaa    720
atcgtgaccg atatcaaaga cggggtatta tccaaccgca ttactgtgcc atccgttcgc    780
acagcgatgt cgaaattgtt gaccccgaat ccggaacttg cggaaacaat tcggacgaaa    840
tgtatgagcc tgagtaattg gtatgggtta attccggccc tgtttccgaa tgccaaatac    900
gtttacggta tcatgaccgg aagcatggaa ccgtatgtac ccaaactccg tcattacgca    960
ggcgatctcc cgttagtcag ccacgactat ggttcaagtg aaggctggat cgcagcgaac   1020
gttacccctc gcctgtcacc cgaagaggca acctttgcgg tgatcccgaa tctgggctat   1080
ttcgaattct tgcctgtctc cgaaaccggc gagggtgaag agaaacccgt gggtctgact   1140
caagtcaaga ttggcgaaga gtatgaagtg gtcattacca actatgcggg tttgtatcgt   1200
tatcgtctgg gcgatgtcgt gaaagtgatt gggttctaca acaacactcc acagctgaaa   1260
ttcatctgcc gtcgcaacct cattctgtcg atcaacatcg acaagaacac agaacgcgat   1320
ctgcagctga gcgttgaatc agccgccaaa cgtctgtcgg aagagaagat tgaggtcatt   1380
gactttagca gctatatcga tgtatcgacc gacccaggac actatgcaat cttctgggaa   1440
atttctggtg aaacgaatga ggatgttctg caggattgct gcaactgtct ggatcgtgcc   1500
tttatcgatg ccggctacgt atcttctcgc aaatgcaaaa cgatcggtgc cctggaactg   1560
cgtgttgttg ctaaaggcac ctttcgcaaa attcaagagc atttcctggg cttgggctcc   1620
agtgctggcc agtttaaaat gccgcgctgt gtgaaaccga gcaacgctaa agtgctgcaa   1680
attctttgtg agaatgttgt gtctagttac tttagcaccg cgttttaa                1728
```

<210> SEQ ID NO 15
<211> LENGTH: 1839
<212> TYPE: DNA
<213> ORGANISM: Arabidopsis thaliana

<400> SEQUENCE: 15

```
atgccagaag ctcccaagaa agaaagcctg gaagtcttcg atctgactct ggatcaaaag     60
aacaaacaga agctgcaact cattgaagag ttaacctcga atgcagatca ggtgcaacgc    120
caggtcctag aggagatttt gacgcggaat gccgatgtcg aatatctgcg acgccatgac    180
ctgaatggcc gcaccgatcg cgaaacgttc aaaaacatca tgccggtgat cacgtatgaa    240
gacattgaac cggagattaa tcgtatcgcg aatggcgata aaagtccgat tctcagctca    300
aaacctatca gcgaatttct gacctcatcc ggtacaagtg gtggcgagcg caaattaatg    360
```

```
ccgacaatcg aagaagaact ggatcgtcgc agcttgctct acagccttct tatgcctgtt     420

atgtctcagt tcgtaccggg tctggagaac gggaaaggca tgtattttct gtttatcaaa     480

tcggagtcca aaacaccggg tggtttaccg gctcgtccag ttctgaccag ctactacaaa     540

tcttcacact tcaaggaacg cccgtatgat ccgtatacga attacacctc tccgaacgag     600

actatcctct gttctgactc ttaccagtca atgtatagtc agatgctgtg tggcctgtgt     660

cagcatcagg aagtcttgcg cgtcggagct gtctttgcca gtgggtttat tcgcgccatc     720

aaattcctcg aaaagcattg gattgaactt gtgcgtgaca tacgtactgg cacgctgtct     780

agcctgatta cggatccaag cgttcgtgaa gcagttgcta aatcctgaa acctcaccc       840

aaattagcgg attttgtaga gttcgaatgc aaaaaaagca gctggcaagg cattattacc     900

cgactgtggc cgaacaccaa atatgtcgac gtgattgtaa cgggcacaat gagccagtat     960

attccaactc tggactatta cagtaatggt ttgcccttgg tatgtaccat gtatgcatcc    1020

tcggaatgct actttggagt gaatctgcgt ccgttatgca aaccgagtga agtgtcgtat    1080

acgctaatcc catccatggc gtacttcgag tttttgcccg tacatcgcaa caatggcgtg    1140

acgaactcca taaacctgcc gaaagccctg accgagaaag agcagcagga attagtggat    1200

ctggttgacg tgaaactggg ccaagagtat gaactggtgg tgaccaccta tgcaggactg    1260

tgccggtacc gtgtggggga tttgctccgg gtaaccggtt ttaagaacaa agcgccgcag    1320

ttcagcttta tttgcaggaa gaatgttgtg ctgtctatcg attctgacaa aacagatgaa    1380

gtggaactgc aaaacgccgt gaaaaacgcg gttactcact tagtgccgtt tgacgcgagc    1440

ctgtccgaat acacctccta tgcggacacg tcaagtattc caggccatta cgtccttttc    1500

tgggaacttt gcttggatgg gaatacccg attcctccga gcgtttttga agattgttgc     1560

ttagcggttg aagaatcgtt taacaccgtc tatcgccaag gtcgtgtatc agacaagtcg    1620

attggcccac tggaaatcaa gatcgttgaa cctggtactt tcgataaact gatggattat    1680

gccataagtc tgggggcaag cattaaccag tacaaaaccc cgagatgcgt caaatttgcg    1740

cccattatcg agctccttaa ctcgcgtgtt gtggattcgt acttctcgcc gaaatgtccg    1800

aaatgggttc ctggtcacaa acagtggggc tccaattaa                           1839
```

<210> SEQ ID NO 16
<211> LENGTH: 1776
<212> TYPE: DNA
<213> ORGANISM: Arabidopsis thaliana

<400> SEQUENCE: 16

```
atggaaacag tggaagctgg ccacgatgac gttattggtt ggttcgaaca cgtttcagaa      60

aatgcatgta aagtgcagtc tgaaaccctg cgtcgtatcc tcgaacttaa ctctggcgta     120

gaatatctgc gtaagtggct gggcacggtg gatgtggaga aaatggatga ttacaccctt     180

gaaaccttat tcaccagcct ggttccgatt gtctcccatg cggatctgga cccttacatt     240

cagcgcattg cggacggcga aacttcaccg ttactgaccc aggaaccaat taccgtcctg     300

tcgctgtcat cgggtacgac agagggtcgc cagaagtatg taccgtttac tcggcatagt     360

gcccaaacca ccctgcaaat ctttcgcttg tcagcggcct atcggtcccg cttttacccg     420

attcgtgaag gcggacgcat tctggaattc atctacgcag gcaaagaatt taaaaccctg     480

ggtgggctga ctgttggtac cgcgacgacc cactattatg ccagcgagga attcaaaacc     540

aaacaggaaa ccaccaaaag cttcacatgc agtccccagg aagtgatttc tggtggtgat     600

tttggtcaat gcacgtattg ccatctcttg cttggccttc attactccag ccaagttgag     660
```

```
ttcgtggcta gcgctttcag ctacaccatt gtacaagcct tcagtttctt tgaggaaatc    720
tggcgtgaga tctgtgcgga tatcaaggag gggaacctga gtagtcgcat tacactgccg    780
aaaatgcgca aagccgtgtt agcgttgatt cgccccaatc cgtcactggc ctctcacatc    840
gaagaaattt gcctggaact ggaaacgaat ctgggttggt ttggcctgat tagcaaactg    900
tggccaaatg cgaagtttat ctcgtcgatc atgacgggca gtatgttacc gtatctgaac    960
aaactccgtc actatgctgg cgggctcccc ttagtttccg cggattatgg gagcacggaa   1020
tcctggattg gcgtaaatgt ggacccacac ttgccacctg aggatgtgtc gttcgcagtc   1080
attccgacct tctcctattt cgagttcatt ccgttatacc gtcgtcaaaa ccagtctgac   1140
atctgcatcg atggcgattt tgtcgaggat aaaccggttc cgttgagcca ggtaaaactg   1200
ggtcaggaat acgagctggt tctcacgact tttacaggac tgtaccgcta tcgcctgggt   1260
gatgttgtgg aagtcaccag ctttcataaa ggaaccccga aactgagctt tatctatcgc   1320
cgtaaactta tcctcacgat taacattgat aagaatacag agaaagatct gcagcgtgtc   1380
gtcgacaaag caagccagtt actgtcgcgt agcacccggg cggaagtggt ggactttacg   1440
tcgcatgccg atgtaattgc acgccctggg cattatgtga tctactggga aattcgtggc   1500
gaagcggatg acaaggcact tgaggaatgt tgccgcgaaa tggatactgc ttttgtggac   1560
tacggctatg ttgttagtcg gcgcatgaac tcaatcgggc ctctggaatt gcgcgtggtc   1620
gagcgtggta cctttggcaa agtggccgaa cgctgcgtag gcaaatgtgg tggattgaac   1680
cagtttaaga ctccgcgctg tacgactaac tctgtcatgc tggacattct gaatgactct   1740
acgatcaaac gctttcgctc gtccgcgtat gattaa                             1776
```

<210> SEQ ID NO 17
<211> LENGTH: 1728
<212> TYPE: DNA
<213> ORGANISM: Arabidopsis thaliana

<400> SEQUENCE: 17

```
atgaaaccga tcttcgacat caacgagact ttcgaaaaac agcttaaaga tctgacatca     60
aatgtcaaga gcattcaaga taacctactg gaagaaataa tcacgcctaa caccaaaact    120
gagtatctgc agcgttttct gattgatcgc tttgacaaag aactgttcaa gaaaaacgtg    180
cctattgtga gctatgagga cattaaaccc taccttgatc gtgtggttaa tggcgaaagc    240
tcggacgtta tttcagcgcg aacgattaca gggtttctcc tgtcaagtgg cacgagtggt    300
ggtgcgcaga agatgatgcc ctggaacaac aagtatctgg acaacctgac cttcatttat    360
gatttgcgca tgcaagtgat caccaaacac gtgaaaggcg tagaagaagg caaaggaatg    420
atgttcctgt ttaccaagca ggaaagcatg acaccaagcg gacttccggc tcgtgtagcc    480
acatcgtcct actttaaatc ggattatttc aaaaatcgtc catccaattg gtattactcg    540
tatacctccc cagatgaagt catcttgtgc ccgaataata cggaatcgct ttattgccat    600
ctgctctgcg gtctagtcca acgcgatgaa gtggttcgca ccggttctat ctttgcgtct    660
gttatggtac gggccattga agttctgaaa aactcgtggg aagagttatg ctcgaacata    720
cggagcggtc acctgagtaa ttgggtcacg gatttaggct gtcagaatag cgtgagtctg    780
gttttaggcg gtccgagacc tgaactggca gacaccatcg aggaaatctg caatcagaac    840
agttggaaag gtatcgtcaa acgcctgtgg cctaatacca agtatattga gacggtagtg    900
actggatcta tggggcagta tgtgccgatg ctgaactatt actgcaatga tttgccgtta    960
```

```
gtgtcgacta cgtatggttc atccgagacc acctttggca tcaaccttga tccgctgtgc   1020

aaaccggaag atgtttccta caccttcatg ccgaacatga gctactttga gttcattccg   1080

atggatggcg gcgataagaa tgatgtagtc gacctggaag atgtcaaact cggttgtacg   1140

tacgaaccgg tggttacgaa ctttgccggt ctgtatcgta tgagggttgg ggatattgtg   1200

ttagtaaccg gcttttacaa caacgcaccg cagttcaaat ttgtccgtcg tgaaaacgtg   1260

gttttaagca ttgacagcga taaaaccaat gaggaagatt tgtttaaagc cgttagccaa   1320

gcgaaattgg ttctggaatc tagtggcctg gatctcaaag actttacctc ctatgctgat   1380

acgtccactt ttccgggtca ttacgtggtg tatctggaag tcgacaccaa ggaaggggaa   1440

gagaaagaga cagcgcagtt tgaactcgat gaggaagctt tgtctacgtg ttgtctggtg   1500

atggaagaga gtctggacaa tgtttacaaa cgctgtcgct ttaaagatgg ctctattggt   1560

cccttggaaa ttcgtgtcgt acgccaaggc acctttgaca gcttaatgga cttcttcatt   1620

tctcaaggcg catcaactgg acagtacaag actccacgct gcatcaaatc agggaaagca   1680

ctgcaggtgc tggaaacctg tgtggtcgcg aaattcttca gcatctaa                1728
```

```
<210> SEQ ID NO 18
<211> LENGTH: 1830
<212> TYPE: DNA
<213> ORGANISM: Arabidopsis thaliana

<400> SEQUENCE: 18

atgattccga gttatgaccc gaatgacacc gaagcagggc tgaaattact ggaagattta     60

accaccaacg cagaagcgat ccaacagcaa gttctgcatc agattctgag ccagaatagc    120

ggcactcagt atttacgtgc cttcttggat ggtgaagctg ataagaacca gcagagcttc    180

aagaataagg ttccggtggt gaattacgac gatgtgaaac ccttcatcca gcgcattgcc    240

gatggcgaat catctgacat tgtgagtgcc caaccgatta ctgagctctt aacctcgtca    300

gggacttctg cgggcaaacc caaactgatg cctagcacag cggaagaact ggaacgcaaa    360

accttctttt actccatgct ggttccaatc atgaacaaat acgtggacgg tttagacgaa    420

ggcaaaggaa tgtaccttct gttcattaag ccggaaatca aaacgccttc cggactgatg    480

gcacgcccag tcctgacgag ctattataag tcccagcatt ttcgtaatcg cccgtttaac    540

aaatacaacg tgtatacatc accggaccag actattctct gccaggatag caaacagtcg    600

atgtactgcc aattgctctg cgggttggtc cagcgttctc atgtcctgcg tgttggtgca    660

gtgtttgcca gcgcgttcct gcgcgctgtc aaattcttag aggatcacta caaagagctt    720

tgcgcggata ttcgtacagg cactgttacc agctggatca cggacagttc ttgccgcgat    780

tccgtactgt cgattctcaa cggcccgaac caggaactgg ctgacgaaat tgaaagcgag    840

tgtgctgaaa agtcttggga ggggattctt cgccggattt ggcccaaagc aaagtatgta    900

gaggtgatcg taaccggttc aatggcccaa tatatcccaa ccctcgaatt ttacagtggc    960

ggcctcccgc tggtttcgac catgtatgcg tcgagtgagt gttactttgg catcaacctg   1020

aaccctctgt gtgatccggc agatgtttcg tacaccctgc tgccaaatat ggcctatttc   1080

gaatttctgc ccgtcgatga caaatcccac gaagagattc acttcgcgac acatagcaat   1140

acggacgatg acgatgatgc tctgaaagaa gatctgattg tgaatttagt caacgtagaa   1200

gtgggtcaat attacgaaat cgtgattacc acgtttactg gcctgtatcg gtatcgggtg   1260

ggtgatatcc tgaaagttac cggttttcat aacaaagccc cacagtttcg ctttgtccag   1320

cgtcgcaatg tggtgctcag cattgataca gacaaaacgt ctgaagaaga tttgttgaac   1380
```

```
gcggtaaccc aagccaagct gaaccatctg cagcatcctt ccagcttgct tctgacggaa   1440

tacacgagct atgcggatac gtctagtatt ccgggccact atgtgctgtt ttgggaactg   1500

aaaccgcgtc actcaaacga tccgccgaaa cttgacgata aaaccatgga ggattgttgc   1560

agtgaagttg aggactgctt agattacgtc tatcgccgtt gtcgcaatcg tgataaatcg   1620

atcggtccac tggaaatccg cgttgtttcg ctgggcacct ttgactccct gatggatttc   1680

tgtgtaagcc aaggcagctc actgaatcag tataaaaccc cgcgttgcgt gaaaagtggt   1740

ggtgcgttgg agatccttga ttctcgtgtc attgggcgct tcttttcaaa acgcgtaccg   1800

caatgggagc ctctgggatt ggattcctaa                                    1830
```

```
<210> SEQ ID NO 19
<211> LENGTH: 1794
<212> TYPE: DNA
<213> ORGANISM: Synechococcus PCC 7335

<400> SEQUENCE: 19

atggtaattc acacgatccc caaggaaatc ctggacagcg tagcctcaac cggtgatgtg     60

tttgcttatc atctgctgcg tagcaccggt gatattggcg aaaccgttct gcagtattta    120

ctgtgtctgg cagcaaaagt caacttgact ggcatcgaac aagacaccta taatgcggat    180

aaagtgcagg aacagctgct gaatgacatc ttacgctctg aaaacaaaac gctgtatggc    240

aagaaataca actttgacag tttaaatgtg gactcgtttc gcagttctct gccgctgacc    300

tcctacgaga attatcgcga gagcattgat aacgttgtgc aaaccggaaa ttattcccaa    360

ttggtttctg agccgatcac gctgttccaa gaatcgtccg gtaccaccgg taaagtcaaa    420

ttgattcctc gcacgaacaa atttacctta tctgcgatgc gggcattcca agccattgaa    480

gcagtcgttc agagccattt ccagaatcct agtagctcaa gtcagcgtgt gctggcgctt    540

gtgaatacat cgccgacgaa actcacccca acgggtattc cccgtggtac aggcacgtca    600

ggtggcctga acgatgcctt acagaaattc aagctggcca actatctgat cgacatcaag    660

tatagttctc cgtcgcctgt ctttctgatt agtaataccg aagccgctta ctactgtcac    720

ttactctttg ggttgctgga tagcgatatc aacgatattt ctgccaactt tgccgctact    780

gtcctgaacg cgatgaaaat tctggagaaa gcttggaccc agctggtaga agatattcgt    840

caggggaaac tttatgcagg cttagatatt gatgaagcta cacgtcgcga actggagatc    900

cgtttgcgcg cgaatccgga gcgtgcacgt gaacttcagg cgtacttcga ggaaggcttc    960

gagggtattc tcccacgcat ctggcctagc ctgagctgca ttcagtgcat tactacaggc   1020

agtatgcaac tgtataccga tgctttacgt tactattcgg gaacggtgcc gttcttttcg   1080

ggtagctatg gcgcgagcga agcgtggatc ggggtaaatc tggatccgga acgcgaacca   1140

cccgcctttg ttgtcacacc gcataccgcg ttcttcgagt ttatcccgca agatgcgatt   1200

gatcaagaac agtccgcaac ggtttgcctt actgatctga aaccgggaga atcctacgaa   1260

gtcgtggtga ccaacatgtc tgggctctac cgctaccgtg tgggcgacgt tgtgcgctgt   1320

gttggttacc accacaagtc gccgatgatt gaattcatgt atcggcgcca aactctgctt   1380

aacctgttcg gcgagaaagt gagcgaggac gtgatctaca gtgcgttgtc aacgactctg   1440

cgtgagtttg gtatggcgat tcaggacatt gactacacat gccgccatga atttgaaggc   1500

accccatggc gctatgttgt atacctggaa ccggcggatt atgagggttg ttcctctcag   1560

catgaaatgg tccagcaacg gctggacgaa gtgctctgca acttatcaga tcgctatcgc   1620
```

```
cagttgcgtg aagtaggaag cattgggagc ctgaaactga aactcgttcg cgaaggcacc   1680

ttttcaggcc tcaaaacccg tctgcttagc caggaacatt ccgatagcca gtttaaaatg   1740

ccgcgcttgc tgacggaaac tgcccttatc tcctttatgg aatcatcgct gtaa         1794
```

<210> SEQ ID NO 20
<211> LENGTH: 1647
<212> TYPE: DNA
<213> ORGANISM: Cystobacter fuscus

<400> SEQUENCE: 20

```
atgcaggcag ccggtcgccg cgataaacag cgctttatcg agcaaacgcg ccatgtagcg     60

cgtgtgaacg ttgacaccct gcgcgcgatt ctgcagcaca atcgcgatac cgattttggt    120

cgccgccatg gtttcgctag cttacgcacc gttgaagatt tccagcgtgc gctcccggtg    180

agcacctatg aaccgtttcg tccctacatg gagcgcattg cgcgcggtga acagaacgtg    240

cttacggcgg atcgcgtcga atacttgggc attacgagcg gtacaaccgg ccaacgcaaa    300

ctcctcccag tctcacggcc acaccttgag aacatgcgtc gcacaatgat gattggccgt    360

gcagtggtga cggaaaaggt tcccgccgct cgccgtccat cacgcgggat gatccttatg    420

aatgcggtac tgcgggaacg cagcgaagga ggtctgttga ccggggcgct gaccgcgatc    480

tctacccact ctatgggtcg tgcggcgagc tttgctttta ccagcccacc agaagccttt    540

cgtctgcgta aacatgcgga tgccctgtat ctgcacttgc tgttcggcct gcgtgagcgt    600

gaactcggca ctttgatggc cccgtttgca tccggactgc ttgacatggt acacttactg    660

gaacgtcgtg gggcagattt ggtcgacgac atcgctcgcg gcgtgttacg tccggaactg    720

gacctggagc ctgaacaacg tcgtctgctg caaagtcgcc tgctgcctga tccggaacgc    780

gcacgtgaag tgtcccaggc actcgaacaa ggcccgcatg gtctgttacg ccgcctgtgg    840

ccccggctgg cgtatgtctc gtcgattact ggtgcttctt tcagcctgta cacccgccag    900

cttacgccgt atttggaagg agtgccgctc tccgctgcgt cctatgtgtc gacggagggc    960

attctgggtg ttccgttgga gctggaacaa gccgtttact gcctcatggt tggcatggcc   1020

ttctttgaat tcatccctga gcgcgaactc gacgcagaat caccgaccac gctgctgccg   1080

gagcagttgg ttgaaggtga agcctacgaa gtggttctga ccacgcaagc aggcctgtat   1140

cgctatcgcc tgggtgatgt cgtgcgcatt gtcggccgct atcatgaggc cccgctgatg   1200

gaattcttat atcgtcgcgg cgccttactg aatctgatgg gcgagaaaac cagtgagcat   1260

gctgctcgtc tggccttgga acaggcatta gccacagagg ggcttctgcc cgcggactac   1320

agtgtagtgg aagaaaccga gactctgcct gggcgctatg cgttgttcgt cgaactgcag   1380

gaaggtgcac gtccacaggg cgcgccggaa cagctgtctc gtgccttaga ggaggcttta   1440

tgtcgcacta acccgtttta cgaagtgatt cggcgttcgg aacgtttagg agcggcccag   1500

ctgcatcgtg tggaaccggg cacatttcag gcactgcggg atgtgcttgt ccagcgcggc   1560

gcgagtccga ctcaggtcaa agttcctcgc gtagttcgtg atgcggaact gcaagggctg   1620

cttcgccaac ggcgcgtaac gggttaa                                      1647
```

<210> SEQ ID NO 21
<211> LENGTH: 1188
<212> TYPE: DNA
<213> ORGANISM: Pseudomonas savastanoi

<400> SEQUENCE: 21

```
atgaccgcgt atgacatgga gaaagagtgg tcacgcattt ccattaccgc agcgaaaatt     60
```

```
caccagaaca atgatttcga ggggttcacg tatcaggatt ttcggaccca tgtgccgatc    120

atggataaag acggctttgc agcgcaaacg gaacgttgtc tggaacgcaa tgaacgcaat    180

tgcctgatcg gatttacctc tggaactagt gggaatatca aacgttgcta ctattactat    240

gactgcgaag ttgatgaaga ttcgtcactt agtaacgtct ttcgctcgaa tggcttcatt    300

ctgccaggtg accgttgtgc gaacttgttc accatcaacc tgttctccgc actgaataac    360

accattacga tgatggccgg taattgtggt gcgcatgtgg taagcgtagg cgatatcacc    420

ctggttacga agagccactt tgaagccctg aactctatca aactgaatgt gttgttaggt    480

gttccctcaa ctattctgca gtttatcaac gcgatgcagc ataatggggt ccacatcaac    540

attgagaagg tggtgtttac cggcgaaagc ctcaaaacct tccagaagaa aattattcgt    600

caagcttttg gcgaacaagt aagcattgtt ggtgtgtatg gttcgtctga aggtggcatt    660

ctggggttta ccaactcccc ttgccatacc gaatacgagt ttctttcaga caaatacttc    720

attgagaaag agggcgattc cattctcatc acgagtctga cccgcgaaaa ctttactccg    780

ctgttacgct atcgtttagg cgacacagcg actctgagca tgaaaggcga caaactgtac    840

ctcacggata ttcaacgcga agatatgagc ttcaacttca tgggcaactt gatcggttta    900

ggcattatcc agcaaacgat caaacagaca ctgggtcgca gcctggaaat tcaggtccat    960

ctttcggtaa ctgaagaacg caaagaactg gttacagtgt ttgtgcaagc aagcgaggtg   1020

gacgaagatg aacgggttcg cattgaaacg gctatcgccg atattccgga tatcaaagag   1080

gcctatcaga agaaccaggg tacagtcagt gtcctccgca aagatgctcg cgattatgcc   1140

gtttctgaac gtggaaagat gttgtacatt attgaccgtc gtaattaa                1188
```

<210> SEQ ID NO 22
<211> LENGTH: 1197
<212> TYPE: DNA
<213> ORGANISM: Pantoea agglomerans

<400> SEQUENCE: 22

```
atgcgcagct atgaccatca accgactttt gtcgaacagc acaatcgcat ctctatcatc     60

agtgggtcga cctttcgtga ttacgagcac ttcgcaagga gcgttccgat ctcgaagtta    120

gtgcgtatgc acgaagtcga gggtaaacaa ggggacgatt cttccgcgaa cttaccgagc    180

ttaattggcg ctaccagtgg tactagcgga aaaatgaaac cagtgcgcat acagttgaaa    240

aatgggggct gttctgtgtc agcctccgaa cgcaacttca tctaccatct gcgcgaacgt    300

cgtgtgtttt tcccgcaaga tgttgtaggc aatctgttca ccattaacct gtttagcaca    360

ctgcatcaga gtgcctgtga catcgtgaaa tattgccaag gcagtattgt gcctgtcggt    420

gatatcgcgt tactgactcg cgatcacttc ctctttctgc aggaagtcga actgtctgtc    480

ctgtttggtg tacctgccac catcattcag tttgtcgaag ctatgctgtc caacaaagtt    540

cccattggaa tcaagaaaat tgtgtttacc ggtgaaacgc ttcgcccatc acaggcggaa    600

tggttgcgct cacgtctagg tcgtaccctg agcattgtag gcctgtatgg tttgagcgag    660

tgcggttttc tgggcttaac cgatgcccaa gactgcgatg aatacacgct gtttaacgac    720

gacttctttt tcgagcagga tccggttcat ggccttcttg tgacctccct ggatccatcc    780

gccaaaaatc gactgattcg atatccgaca ggtgatggcg tagaactgac gtttcacaat    840

aaacagctga aaatgcggat tatggcccgg aaagacctcc tgttcaactt cgtcgggaat    900

ctcatttcgg tggagagcat tgctgcaacg gttgcagagt caataccgga gagctttatt    960
```

-continued

```
caactagtga tccgctcgga aaaaggccag caagaattgc ttctggttaa cgttgcaggc   1020
aagaacttgc agacgcaaca gctcgaactg attgcgcaga aactgcgtgc acgtcccgaa   1080
ttggcggaag tgtatcagaa gcagcgtggc agattagaag tgcattcggt agcggagaat   1140
gcgtttgttc tgagtgcgcg tggaaaacat cagttcgttg tggatgaacg cgaataa      1197
```